US011260090B2

(12) United States Patent
Bruce et al.

(10) Patent No.: US 11,260,090 B2
(45) Date of Patent: Mar. 1, 2022

(54) MODIFIED ARENAVIRUS

(71) Applicant: University of Vermont and State Agricultural College, Burlington, VT (US)

(72) Inventors: Emily Adaline Bruce, Hinesburg, VT (US); Jason William Botten, Williston, VT (US); Christopher Michael Ziegler, Winooski, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 330 days.

(21) Appl. No.: 16/082,768

(22) PCT Filed: Mar. 8, 2017

(86) PCT No.: PCT/US2017/021390
§ 371 (c)(1),
(2) Date: Sep. 6, 2018

(87) PCT Pub. No.: WO2017/156146
PCT Pub. Date: Sep. 14, 2017

(65) Prior Publication Data
US 2019/0083553 A1    Mar. 21, 2019

Related U.S. Application Data

(60) Provisional application No. 62/305,109, filed on Mar. 8, 2016.

(51) Int. Cl.
*C12N 7/00*    (2006.01)
*A61K 35/76*    (2015.01)
(Continued)

(52) U.S. Cl.
CPC .............. *A61K 35/76* (2013.01); *A61P 37/04* (2018.01); *C12N 7/00* (2013.01); *C12N 15/86* (2013.01);
(Continued)

(58) Field of Classification Search
None
See application file for complete search history.

(56) References Cited

U.S. PATENT DOCUMENTS

2003/0092145 A1*   5/2003   Jira ...................... A61K 39/015
                                                435/173.3
2003/0105277 A1    6/2003   Morham et al.
(Continued)

FOREIGN PATENT DOCUMENTS

WO        2003/051835 A2    6/2003
WO    WO-2009083210 A1 *    7/2009    ............. C12N 15/86
WO        2015/082570 A1    6/2015

OTHER PUBLICATIONS

Huang et al., "Highly Pathogenic New World and Old World Human Arenaviruses Induce Distinct Interferon Responses in Human Cells,", Journal of Virology, vol. 89, No. 14: 7070-7088 (Year: 2015).*

(Continued)

*Primary Examiner* — M Franco G Salvoza
(74) *Attorney, Agent, or Firm* — Hodgson Russ LLP

(57) ABSTRACT

Provided are modified arenaviruses and populations thereof, wherein the modified arenaviruses include i) an introduced PPXY domain; ii) an increased number of PPXY domains; iii) a substituted amino acid in place of S41 in a viral Z protein that is not a substrate for a serine or tyrosine kinase, or a combination of i)-iii). A PPXY domain can include a phosphomimetic replacement of the Y amino acid. Modified Old World and New World arenaviruses are included. Arenavirus production is provided using cell cultures that contain a kinase inhibitor that inhibits a kinase that can phosphorylate the Y amino acid of the PPXY domain, or by cells that have disrupted kinase gene expression, or by cells that have a disrupted ESCRT system. Also provided are pharmaceutical formulations that contain modified arenaviruses, and methods of using such formulations for stimulating an (Continued)

immune response hat is fully or partially protective against arenavirus infection.

6 Claims, 24 Drawing Sheets

Specification includes a Sequence Listing.

(51) Int. Cl.
    *A61P 37/04*      (2006.01)
    *C12N 15/86*      (2006.01)

(52) U.S. Cl.
    CPC .............. *C12N 2760/10021* (2013.01); *C12N 2760/10022* (2013.01); *C12N 2760/10023* (2013.01); *C12N 2760/10032* (2013.01); *C12N 2760/10051* (2013.01)

(56) References Cited

U.S. PATENT DOCUMENTS

2010/0272706 A1* 10/2010 Mercer ................... A61P 31/12
    424/130.1
2017/0174678 A1* 6/2017 Harty ................... A61K 31/454

OTHER PUBLICATIONS

Moraz, M.L., et al., Cell entry of Lassa virus induces tyrosine phosphorylation of dystroglycan, Cellular Microbiology, Dec. 20, 2012, vol. 15, No. 5, pp. 689-700.

Ziegler, C.M., et al., The Lymphocytic Choriomeningitis Virus Matrix Protein PPXY Late Domain Drives the Production of Defective Interfering Particles, PLoS Pathogens, Mar. 24, 2016, vol. 12, No. 3, e1005501, pp. 1-29.

* cited by examiner

Fig 1
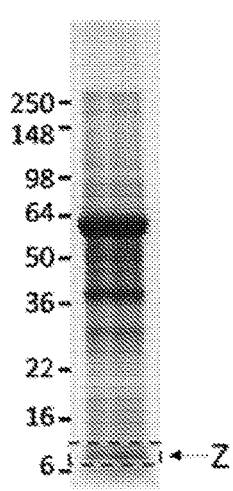
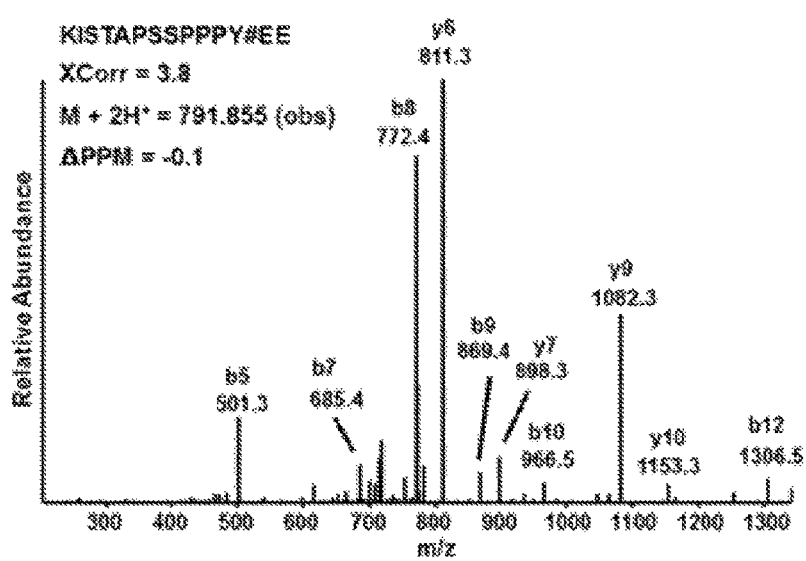
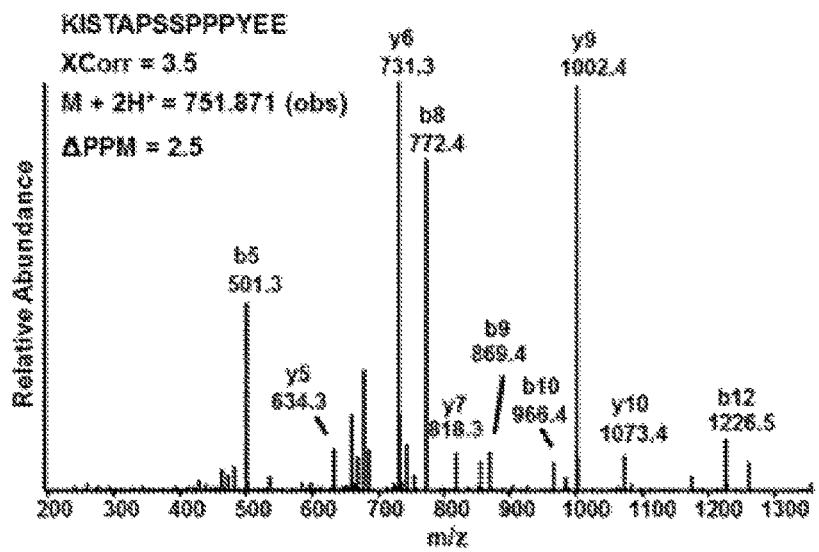

Fig 1 (continued)
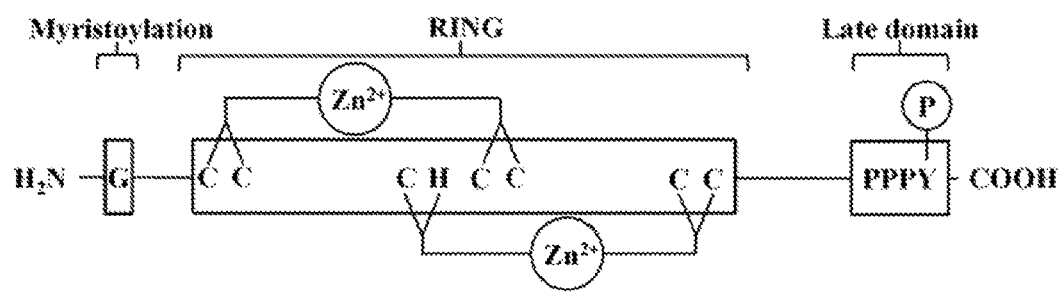
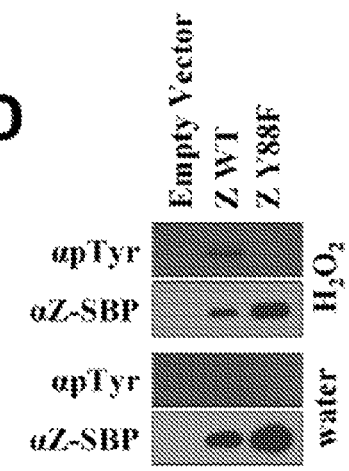
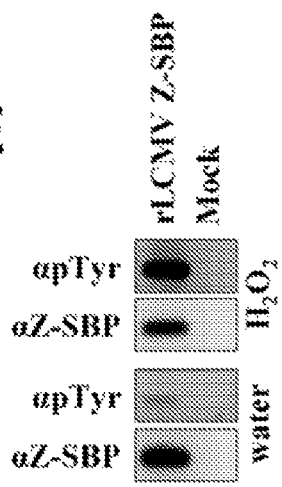

Fig 2

PPPYEE – SEQ ID NO:2
PPPYSP – SEQ ID NO:3
PPPYTP – SEQ ID NO:4
PPPED – SEQ ID NO:5

A

| Sequence Alignment | | |
|---|---|---|
| Virus (strain) | | Peptide Sequence |
| Old World | LCMV-Armstrong | PPPYEE |
| | LCMV-WE | PPPYEE |
| | Lassa Virus-Josiah | PPPYSP |
| | Dandenong virus | PPPYEE |
| | Mobala Virus | PPPYSP |
| | Mopeia Virus-Mozambique | PPPYTP |
| | Ippy Virus | PPPYSP |
| | Lujo Virus | PP- |
| New World | Junín Virus | PPP- |
| | Guanarito Virus | PPE- |
| | Machupo Virus | PPP- |
| | Sabiá Virus | PPPED- |

B

Virus Titer (PFU/mL) vs Hours After Infection

- rLCMV WT
- rLCMV Z-Y88F
- rLCMV Z-Y88E
- rLCMV Z-Y88A

| Hours After Infection | 2-Way ANOVA Summary for Y88 Mutant Growth Curves | | | | | |
|---|---|---|---|---|---|---|
| | WT v. Y88F | WT v. Y88E | WT v. Y88A | Y88F v. Y88E | Y88F v. Y88A | Y88E v. Y88A |
| 1 | ** | n.s. | n.s. | n.s. | n.s. | n.s. |
| 12 | **** | **** | **** | *** | n.s. | *** |
| 24 | **** | **** | **** | ** | n.s. | ** |
| 36 | **** | * | **** | **** | n.s. | ** |
| 48 | n.s. | n.s. | n.s. | n.s. | n.s. | n.s. |
| 72 | **** | **** | **** | n.s. | n.s. | n.s. |

Fig 2 (continued)
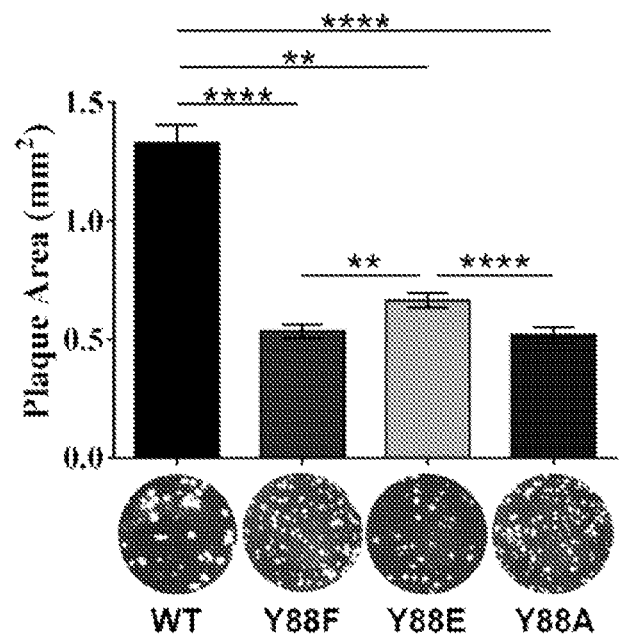
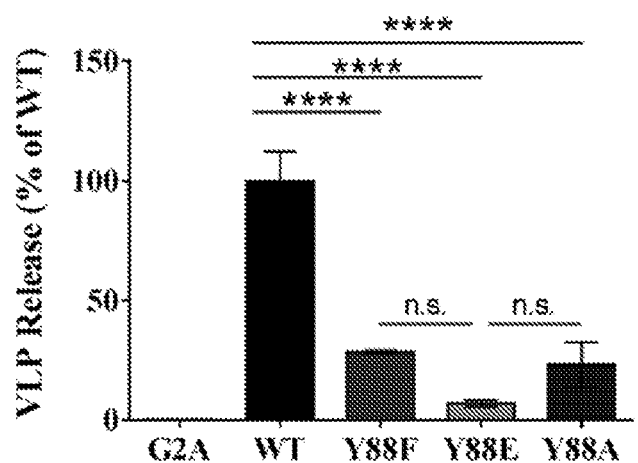

Fig 5  A

LCMV DI Titer (PFU₅₀/mL)

Challenge Virus: LCMV, JUNV, VSV

Dilution of UV-treated LCMV DI: Neat, 1:5, 1:25, 1:125, 1:625, 1:3,125

- Media
- (no UV) LCMV
- UV-LCMV
- 50 PFU LCMV
- UV-LCMV + 50 PFU LCMV
- 50 PFU JUNV C#1
- UV-LCMV + 50 PFU JUNV C#1
- S VSV
- UV-LCMV + 50 PFU VSV

Fig 5 (continued)
B
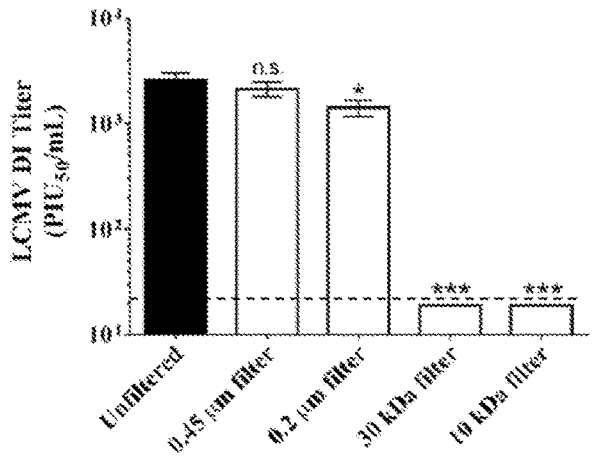
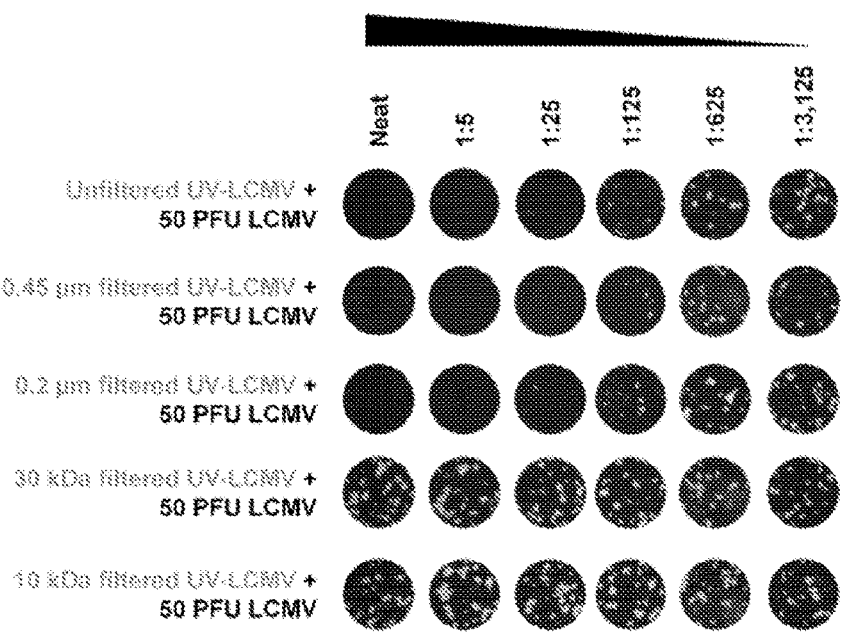
C
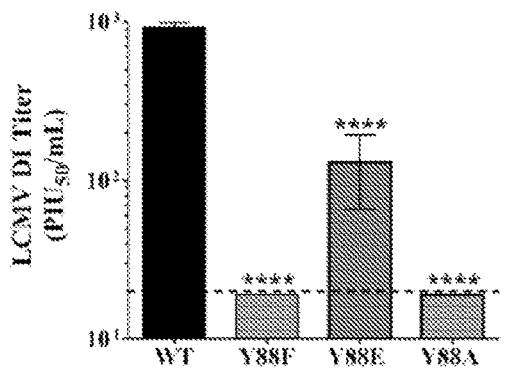

Fig 6 (continued)
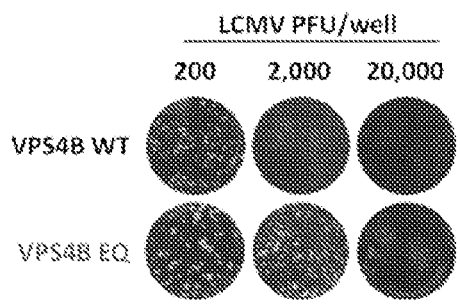
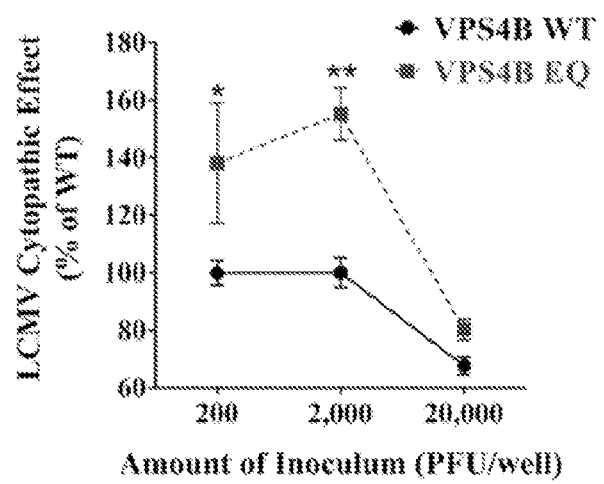
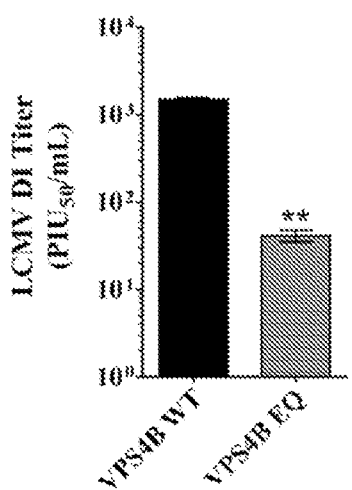

Fig 8

KISTAPSSPPPYEE – SEQ ID NO:6

A

Fragment Ions z=1

Sequence: KISTAPPSSPPPY*EE

| Seq | # | b | y | +1 |
|---|---|---|---|---|
| K | 1 | 129.020 | --- | 14 |
| I | 2 | 242.186 | 1454.609 | 13 |
| S | 3 | 329.218 | 1341.525 | 12 |
| T | 4 | 430.266 | 1254.493 | 11 |
| A | 5 | 501.303 | 1153.445 | 10 |
| P | 6 | 598.356 | 1082.408 | 9 |
| S | 7 | 685.388 | 985.355 | 8 |
| S | 8 | 772.420 | 898.323 | 7 |
| P | 9 | 869.473 | 811.291 | 6 |
| P | 10 | 966.525 | 714.238 | 5 |
| P | 11 | 1063.578 | 617.185 | 4 |
| Y* | 12 | 1306.608 | 520.133 | 3 |
| E | 13 | 1435.650 | 277.103 | 2 |
| E | 14 | --- | 148.060 | 1 |

B

Fragment Ions z=1

Sequence: KISTAPSSPPPYEE

| Seq | # | b | y | +1 |
|---|---|---|---|---|
| K | 1 | 129.020 | --- | 14 |
| I | 2 | 242.186 | 1374.642 | 13 |
| S | 3 | 329.218 | 1261.558 | 12 |
| T | 4 | 430.266 | 1174.526 | 11 |
| A | 5 | 501.303 | 1073.479 | 10 |
| P | 6 | 598.356 | 1002.441 | 9 |
| S | 7 | 685.388 | 905.389 | 8 |
| S | 8 | 772.420 | 818.357 | 7 |
| P | 9 | 869.473 | 731.325 | 6 |
| P | 10 | 966.525 | 634.272 | 5 |
| P | 11 | 1063.578 | 537.219 | 4 |
| Y | 12 | 1226.642 | 440.166 | 3 |
| E | 13 | 1355.684 | 277.103 | 2 |
| E | 14 | --- | 148.060 | 1 |

C

| Number | XCorr | Peptide |
|---|---|---|
| 1 | 2.503 | K.ISTAPSSPPPY#EE.- |
| 2 | 3.392 | K.ISTAPSSPPPYEE.- |
| 3 | 3.021 | K.ISTAPSSPPPYEE.- |
| 4 | 2.97 | K.ISTAPSSPPPYEE.- |
| 5 | 2.944 | K.ISTAPSSPPPYEE.- |
| 6 | 2.854 | K.ISTAPSSPPPYEE.- |
| 7 | 2.802 | K.ISTAPSSPPPYEE.- |
| 8 | 2.788 | K.ISTAPSSPPPYEE.- |
| 9 | 2.753 | K.ISTAPSSPPPYEE.- |
| 10 | 2.814 | K.ISTAPSSPPPYEE.- |
| 11 | 2.492 | K.ISTAPSSPPPYEE.- |
| 12 | 2.488 | K.ISTAPSSPPPYEE.- |

Fig 13
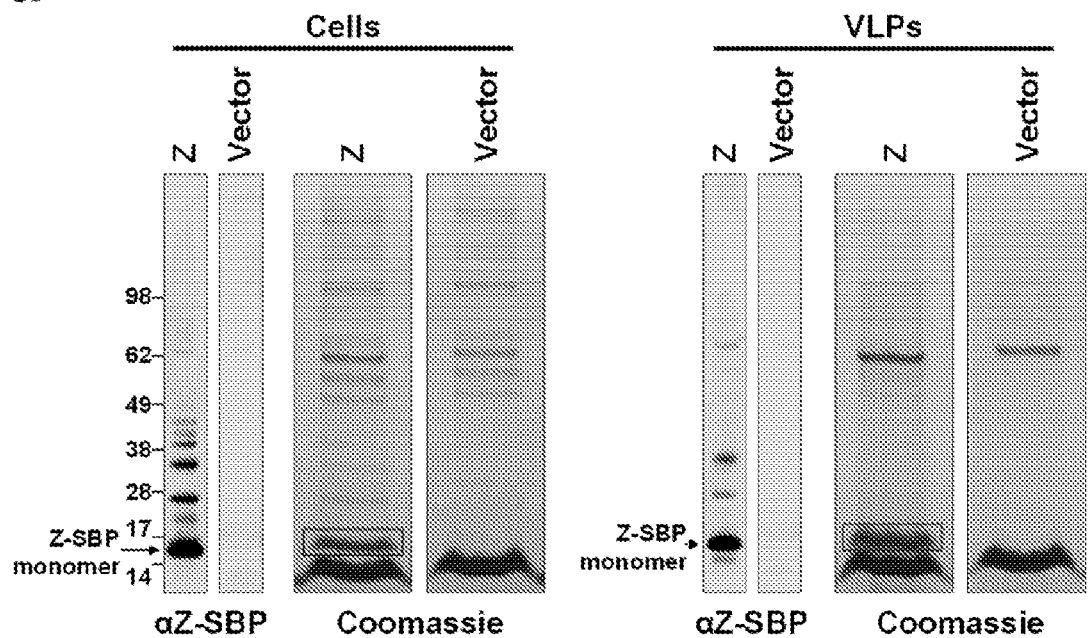
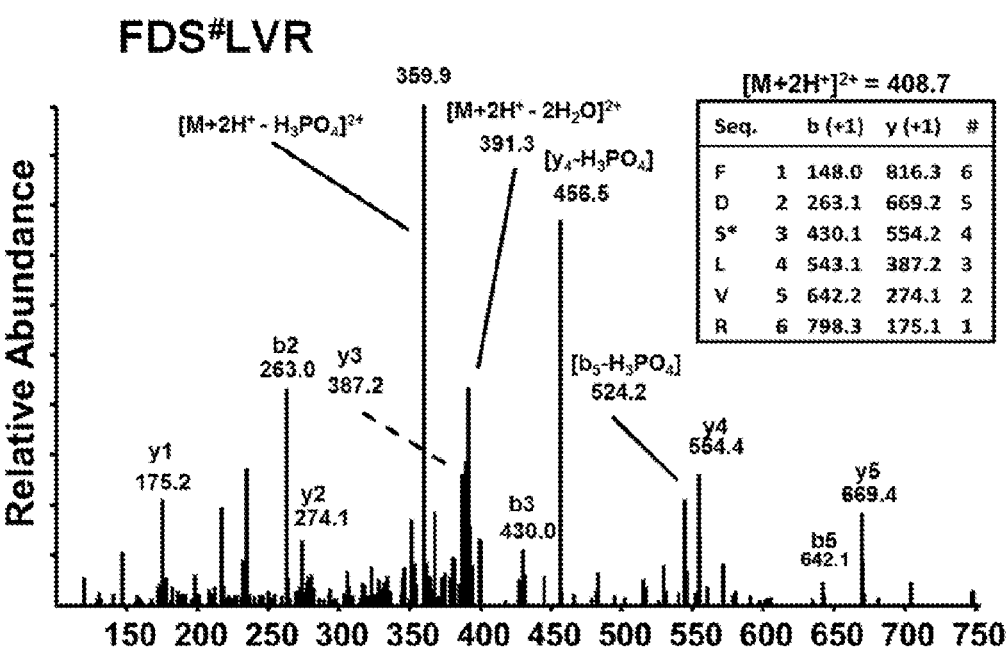

Myristoylation — RING Domain — Late Domain

S41 (P), Zn²⁺, Y88 (P)

H₂N–G–C–C–FDSLVRC–H–C–C–C–C–PPPY–COOH

Zn²⁺ d

| | Sequence Alignment | |
|---|---|---|
| | Virus (strain) | Peptide Sequence |
| Old World | LCMV-Armstrong | WQKFDSLVRCH |
| | LCMV-WE | WQKFDSLVRCH |
| | Lassa Josiah | WFENKGLVECN |
| | Dandenong | WQRFDSLVRCH |
| | Mobala | WFERKGLIKCQ |
| | Mopeia | WFERRGLVKCY |
| | Ippy | WFERRSLVACN |
| | Lujo | WKSKKALVKCY |
| New World | Junin | WFADTNLITCN |
| | GTOV | WFADKNLIKCS |
| | MACV | WFADTNLITCN |
| | SABV | WFANTNLIKCS |

WQKFDSLVRCH (SEQ ID NO:7)
WFENKGLVECN (SEQ ID NO:8)
WQRFDSLVRCH (SEQ ID NO:9)
WFERKGLIKCQ (SEQ ID NO:10)
WFERRGLVKCY (SEQ ID NO:11)
WFERRSLVACN (SEQ ID NO:12)
WKSKKALVKCY (SEQ ID NO:13)
WFADTNLITCN (SEQ ID NO:14)
WFADKNLIKCS (SEQ ID NO:15)
WFANTNLIKCS (SEQ ID NO:16)

Fig 14

Fig 14 (continued)
c
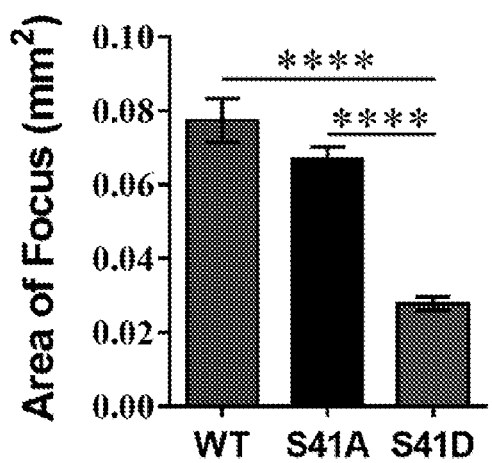
d
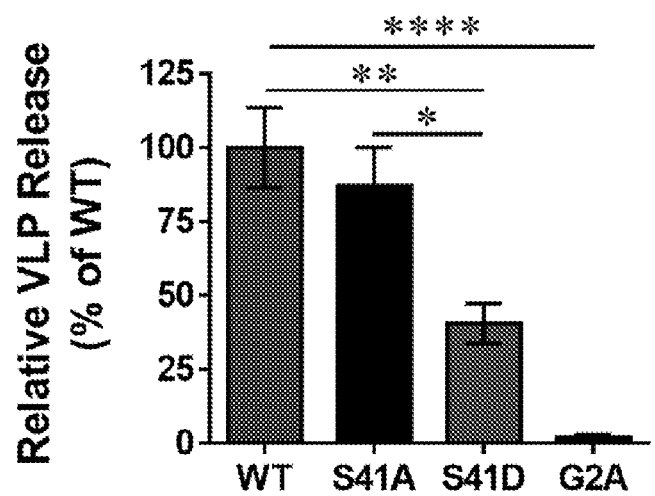

SEQUENCE LISTING

```
<160> NUMBER OF SEQ ID NOS: 42

<210> SEQ ID NO 1
<211> LENGTH: 90
<212> TYPE: PRT
<213> ORGANISM: Arenavirus

<400> SEQUENCE: 1

Met Gly Gln Gly Lys Ser Arg Glu Glu Lys Gly Thr Asn Ser Thr Asn
1               5                   10                  15

Arg Ala Glu Ile Leu Pro Asp Thr Thr Tyr Leu Gly Pro Leu Ser Cys
                20                  25                  30

Lys Ser Cys Trp Gln Lys Phe Asp Ser Leu Val Arg Cys His Asp His
            35                  40                  45

Tyr Leu Cys Arg His Cys Leu Asn Leu Leu Leu Ser Val Ser Asp Arg
        50                  55                  60

Cys Pro Leu Cys Lys Tyr Pro Leu Pro Thr Arg Leu Lys Ile Ser Thr
65                  70                  75                  80

Ala Pro Ser Ser Pro Pro Tyr Glu Glu
                85                  90

<210> SEQ ID NO 2
<211> LENGTH: 6
<212> TYPE: PRT
<213> ORGANISM: Arenavirus
```

-continued

<400> SEQUENCE: 2

Pro Pro Pro Tyr Glu Glu
1 5

<210> SEQ ID NO 3
<211> LENGTH: 6
<212> TYPE: PRT
<213> ORGANISM: Arenavirus

<400> SEQUENCE: 3

Pro Pro Pro Tyr Ser Pro
1 5

<210> SEQ ID NO 4
<211> LENGTH: 6
<212> TYPE: PRT
<213> ORGANISM: Arenavirus

<400> SEQUENCE: 4

Pro Pro Pro Tyr Thr Pro
1 5

<210> SEQ ID NO 5
<211> LENGTH: 5
<212> TYPE: PRT
<213> ORGANISM: Arenavirus

<400> SEQUENCE: 5

Pro Pro Pro Glu Asp
1 5

<210> SEQ ID NO 6
<211> LENGTH: 14
<212> TYPE: PRT
<213> ORGANISM: Arenavirus

<400> SEQUENCE: 6

Lys Ile Ser Thr Ala Pro Ser Ser Pro Pro Pro Tyr Glu Glu
1 5 10

<210> SEQ ID NO 7
<211> LENGTH: 11
<212> TYPE: PRT
<213> ORGANISM: Arenavirus

<400> SEQUENCE: 7

Trp Gln Lys Phe Asp Ser Leu Val Arg Cys His
1 5 10

<210> SEQ ID NO 8
<211> LENGTH: 11
<212> TYPE: PRT
<213> ORGANISM: Arenavirus

<400> SEQUENCE: 8

Trp Phe Glu Asn Lys Gly Leu Val Glu Cys Asn
1 5 10

<210> SEQ ID NO 9
<211> LENGTH: 11
<212> TYPE: PRT
<213> ORGANISM: Arenavirus

<400> SEQUENCE: 9

Trp Gln Arg Phe Asp Ser Leu Val Arg Cys His
1               5                   10

<210> SEQ ID NO 10
<211> LENGTH: 11
<212> TYPE: PRT
<213> ORGANISM: Arenavirus

<400> SEQUENCE: 10

Trp Phe Glu Arg Lys Gly Leu Ile Lys Cys Gln
1               5                   10

<210> SEQ ID NO 11
<211> LENGTH: 11
<212> TYPE: PRT
<213> ORGANISM: Arenavirus

<400> SEQUENCE: 11

Trp Phe Glu Arg Arg Gly Leu Val Lys Cys Tyr
1               5                   10

<210> SEQ ID NO 12
<211> LENGTH: 11
<212> TYPE: PRT
<213> ORGANISM: Arenavirus

<400> SEQUENCE: 12

Trp Phe Glu Arg Arg Ser Leu Val Ala Cys Asn
1               5                   10

<210> SEQ ID NO 13
<211> LENGTH: 11
<212> TYPE: PRT
<213> ORGANISM: Arenavirus

<400> SEQUENCE: 13

Trp Lys Ser Lys Lys Ala Leu Val Lys Cys Tyr
1               5                   10

<210> SEQ ID NO 14
<211> LENGTH: 11
<212> TYPE: PRT
<213> ORGANISM: Arenavirus

<400> SEQUENCE: 14

Trp Phe Ala Asp Thr Asn Leu Ile Thr Cys Asn
1               5                   10

<210> SEQ ID NO 15
<211> LENGTH: 11
<212> TYPE: PRT
<213> ORGANISM: Arenavirus

<400> SEQUENCE: 15

Trp Phe Ala Asp Lys Asn Leu Ile Lys Cys Ser
1               5                   10

<210> SEQ ID NO 16
<211> LENGTH: 11
<212> TYPE: PRT
<213> ORGANISM: Arenavirus

<400> SEQUENCE: 16

Trp Phe Ala Asn Thr Asn Leu Ile Lys Cys Ser
1               5                   10

<210> SEQ ID NO 17
<211> LENGTH: 90
<212> TYPE: PRT
<213> ORGANISM: Arenavirus

<400> SEQUENCE: 17

Met Gly Gln Gly Lys Ser Lys Glu Arg Asp Thr Ser Asn Thr Gly
1               5                   10                  15

Arg Ala Glu Leu Leu Pro Asp Thr Thr Tyr Leu Gly Pro Le

```
                85                  90

<210> SEQ ID NO 20
<211> LENGTH: 99
<212> TYPE: PRT
<213> ORGANISM: Arenavirus

<400> SEQUENCE: 20

Met Gly Gln Lys Pro Ser Lys Pro Lys Ala Pro Pro Thr Thr Tyr Glu
1               5                   10                  15

Ser Pro Arg Ser Ser Leu Thr Pro Asp Ala Thr Gly Phe Gly Pro Glu
            20                  25                  30

Phe Cys Lys Ser Cys Trp Phe Glu Arg Lys Gly Leu Ile Lys Cys Gln
        35                  40                  45

Asn His Tyr Leu Cys Met Thr Cys Leu Thr Leu Leu Leu Thr Val Ser
    50                  55                  60

Asn Arg Cys Pro Val Cys Lys Tyr Pro Leu Pro Thr Lys Leu Arg Leu
65                  70                  75                  80

Glu Lys Ser Pro Thr Ala Pro Pro Pro Glu Ala Thr Asn Pro Pro Pro
                85                  90                  95

Tyr Ser Pro

<210> SEQ ID NO 21
<211> LENGTH: 103
<212> TYPE: PRT
<213> ORGANISM: Arenavirus

<400> SEQUENCE: 21

Met Gly Lys Ser Gln Ser Lys Ser Ser Pro His Asn Lys Pro Pro Glu
1               5                   10                  15

Pro Glu Ala Pro Arg His Pro Val Ile Pro Asp Ala Arg Gly Thr Gly
            20                  25                  30

Pro Glu Phe Cys Lys Ser Cys Trp Phe Glu Arg Arg Gly Leu Val Lys
        35                  40                  45

Cys Tyr Asp His Tyr Leu Cys Leu Asn Cys Leu Thr Leu Leu His Thr
    50                  55                  60

Val Ser Asp Arg Cys Pro Ile Cys Lys His Thr Leu Pro Leu Lys Leu
65                  70                  75                  80

Glu Leu Gln Thr Gln Pro Thr Ala Pro Pro Glu His Pro Pro Asn Gln
                85                  90                  95

Gln Pro Pro Pro Tyr Thr Pro
            100

<210> SEQ ID NO 22
<211> LENGTH: 101
<212> TYPE: PRT
<213> ORGANISM: Arenavirus

<400> SEQUENCE: 22

Met Gly Gln Asn Gln Ser Arg Asp Lys Gln Lys Ala Ile Gln Asn Gln
1               5                   10                  15

Pro Lys Asp Thr Gly Asn Arg Ala Asp Ile Ile Pro Asp Ala Thr Gly
            20                  25                  30

Met Gly Pro Glu Phe Cys Lys Ser Cys Trp Phe Glu Arg Arg Ser Leu
        35                  40                  45

Val Ala Cys Asn Asn His Tyr Leu Cys Met Asn Cys Leu Thr Leu Leu
    50                  55                  60
```

-continued

```
Leu Ser Val Ser Glu Arg Cys Pro Ile Cys Lys Leu Pro Leu Pro Gln
65                  70                  75                  80

Lys Leu Lys Leu Thr Ser Ser Pro Ser Ala Pro Pro Ser Pro Ser Pro
                85                  90                  95

Pro Pro Tyr Ser Pro
            100

<210> SEQ ID NO 23
<211> LENGTH: 95
<212> TYPE: PRT
<213> ORGANISM: Arenavirus

<400> SEQUENCE: 23

Met Gly Gln Arg His Ser Ser Gly Ser Gly Gln Pro Asn Pro Lys Pro
1               5                   10                  15

Ser Asp Ser Asp His Glu Ala Arg Arg Ser Glu Leu His Ser Asp Ala
                20                  25                  30

Ser His Leu Gly Pro Leu Asn Cys Lys Ser Cys Trp L

```
                50                  55                  60
Val Met Leu Lys Asn Ser Asp Leu Cys Asn Ile Cys Trp Glu Gln Leu
 65                  70                  75                  80

Pro Thr Cys Ile Thr Val Pro Glu Glu Pro Ser Ala Pro Pro Glu
                 85                  90                  95
```

<210> SEQ ID NO 26
<211> LENGTH: 94
<212> TYPE: PRT
<213> ORGANISM: Arenavirus

<400> SEQUENCE: 26

```
Met Gly Asn Cys Asn Lys Pro Pro Lys Arg Pro Pro Asn Thr Gln Thr
  1               5                  10                  15

Ser Ser Asn Gln Pro Ser Ala Glu Phe Arg Arg Thr Ala Pro Pro Ser
                 20                  25                  30

Leu Tyr Gly Arg Tyr Asn Cys Lys Cys Cys Trp Phe Ala Asp Thr Asn
                 35                  40                  45

Leu Ile Thr Cys Asn Asp His Tyr Leu Cys Leu Arg Cys His Gln Thr
 50                  55                  60

Met Leu Arg Asn Ser Glu Leu Cys His Ile Cys Trp Lys Pro Leu Pro
 65                  70                  75                  80

Thr Ser Ile Thr Val Pro Val Glu Pro Ser Ala Pro Pro Pro
                 85                  90
```

<210> SEQ ID NO 27
<211> LENGTH: 100
<212> TYPE: PRT
<213> ORGANISM: Arenavirus

<400> SEQUENCE: 27

```
Met Gly Asn Ser Lys Ser Lys Ser Lys Leu Ser Ala Asn Gln Tyr Glu
  1               5                  10                  15

Gln Gln Thr Val Asn Ser Thr Lys Gln Val Ala Ile Leu Lys Arg Gln
                 20                  25                  30

Ala Glu Pro Ser Leu Tyr Gly Arg His Asn Cys Arg Cys Cys Trp Phe
                 35                  40                  45

Ala Asn Thr Asn Leu Ile Lys Cys Ser Asp His Tyr Ile Cys Leu Lys
 50                  55                  60

Cys Leu Asn Ile Met Leu Gly Lys Ser Ser Phe Cys Asp Ile Cys Gly
 65                  70                  75                  80

Glu Glu Leu Pro Thr Ser Ile Val Val Pro Ile Glu Pro Ser Ala Pro
                 85                  90                  95

Pro Pro Glu Asp
                100
```

<210> SEQ ID NO 28
<211> LENGTH: 38
<212> TYPE: PRT
<213> ORGANISM: Artificial Sequence
<220> FEATURE:
<223> OTHER INFORMATION: Artificial peptide

<400> SEQUENCE: 28

```
Met Asp Glu Lys Thr Thr Gly Trp Arg Gly Gly His Val Val Glu Gly
  1               5                  10                  15

Leu Ala Gly Glu Leu Glu Gln Leu Arg Ala Arg Leu Glu His His Pro
                 20                  25                  30
```

Gln Gly Gln Arg Glu Pro
          35

<210> SEQ ID NO 29
<211> LENGTH: 58
<212> TYPE: DNA
<213> ORGANISM: Artificial Sequence
<220> FEATURE:
<223> OTHER INFORMATION: Primer

<400> SEQUENCE: 29
acaagtttgt acaaaaaagc aggctgatat cgccaccatg ggtcaaggca agtccaga        58

<210> SEQ ID NO 30
<211> LENGTH: 39
<212> TYPE: DNA
<213> ORGANISM: Artificial Sequence
<220> FEATURE:
<223> OTHER INFORMATION: Primer

<400> SEQUENCE: 30
acctccacct ccagctgcct cttcgtaggg aggtggaga        39

<210> SEQ ID NO 31
<211> LENGTH: 39
<212> TYPE: DNA
<213> ORGANISM: Artificial Sequence
<220> FEATURE:
<223> OTHER INFORMATION: Primer

<400> SEQUENCE: 31
gcagctggag gtggaggtat ggacgaaaaa accaccggt        39

<210> SEQ ID NO 32
<211> LENGTH: 50
<212> TYPE: DNA
<213> ORGANISM: Artificial Sequence
<220> FEATURE:
<223> OTHER INFORMATION: Primer

<400> SEQUENCE: 32
accactttgt acaagaaagc tgggtcttac ggttcacgct gaccctgcgg        50

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
atagtacaaa cagggccgaa atcc        24

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
tttgttgggt tcagagataa gtgt        24

<210> SEQ ID NO 35
<211> LENGTH: 24
<212> TYPE: DNA

```
<213> ORGANISM: Artificial Sequence
<220> FEATURE:
<223> OTHER INFORMATION: Primer

<400> SEQUENCE: 35
cagggtgcaa gtggtgtggt aaga                                              24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tgggactgag tttcgagcat tacg                                              24

<210> SEQ ID NO 37
<211> LENGTH: 17
<212> TYPE: DNA
<213> ORGANISM: Artificial Sequence
<220> FEATURE:
<223> OTHER INFORMATION: Primer

<400> SEQUENCE: 37
cgctggcctg ggtgaat                                                      17

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
ggccttgtat ggagtagcac ctt                                               23

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
atgggaaaac acaacaattg atctc                                             25

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
ggtctgtgag atatcaagtg gtagaatg                                          28

<210> SEQ ID NO 41
<211> LENGTH: 15
<212> TYPE: DNA
<213> ORGANISM: Artificial Sequence
<220> FEATURE:
<223> OTHER INFORMATION: Primer

<400> SEQUENCE: 41
ctgcaggttt ctcgc                                                        15
```

```
<210> SEQ ID NO 42
<211> LENGTH: 25
<212> TYPE: DNA
<213> ORGANISM: Artificial Sequence
<220> FEATURE:
<223> OTHER INFORMATION: Primer

<400> SEQUENCE: 42
ctgaagaata ccacctatta tacca                                              25
```

MODIFIED ARENAVIRUS

CROSS REFERENCE TO RELATED APPLICATIONS

This application claims priority to U.S. provisional patent application No. 62/305,109, filed Mar. 8, 2016, the disclosure of which is incorporated herein by reference.

STATEMENT REGARDING FEDERALLY SPONSORED RESEARCH

This invention was made with government support under National Institutes of Health grants numbers R21 AI088059 and P20RR021905. The government has certain rights in the invention.

BACKGROUND OF THE DISCLOSURE

Arenaviruses cause severe diseases in humans but establish asymptomatic, lifelong infections in rodent reservoirs. Persistently-infected rodents harbor high levels of defective interfering (DI) particles, which are thought to be important for establishing persistence and mitigating virus-induced cytopathic effect. Little is known about what drives the production of DI particles. There is an ongoing and unmet need for compositions and methods that are useful in the context of interfering with arenavirus replication cycle and infection. The present disclosure pertains to this need.

SUMMARY OF THE DISCLOSURE

The present disclosure relates to modified arenaviruses, and compositions and methods for manipulating generation of DI particles relative to infectious particles. As is known in the art, Arenaviruses are enveloped viruses with a single-stranded, bi-segmented RNA wherein a small (S) segment encodes the nucleoprotein (NP) and glycoprotein (GP) while the large (L) segment encodes the RNA-dependent RNA polymerase (L) and the matrix protein (Z). Z is understood to participate in viral particle release via so-called viral late domains, one of which is the sequence amino acid sequence PPXY, wherein X can be any amino acid, specific examples of which are provided below in the detailed description. DI particles are typically produced with standard, infectious virus during the normal course of infection, and arenaviruses generate high levels of DI particles in cell culture and in host rodents. The present disclosure is based in part on manipulation of DI particle generation using the PPXY late domain, and in particular takes advantage of the discovery that the terminal tyrosine in the PPXY motif is reversibly phosphorylated that this posttranslational modification affects DI particle formation. Accordingly, the present disclosure includes a description of a previously unknown role for the PPXY late domain that is exploited to alter DI particle production. The disclosure also demonstrates that LCMV Z protein is phosphorylated at serine 41 and that a recombinant (r)LCMV bearing a phosphomimetic mutation (S41D) was impaired in infectious and defective interfering (DI) particle release while a nonphosphorylatable mutant (S41A) was not. The S41D mutant therefore disproportionately impairs the ability to release DI particles relative to infectious particles. Accordingly, the disclosure in various embodiments provides viral genome and protein modifications, and viral production conditions and methods, which leverage the discoveries that phosphorylation at Y88 of LCMV Z increases DI particle production, whereas phosphorylation of LCMV Z S41 represses it. The disclosure accordingly provides modified viruses, expression vectors encoding them, compositions comprising them, and methods of making and using them to provide compositions and methods that are useful for a variety of purposes, including but not necessarily limited to vaccines and vaccine-based approaches. In non-limiting examples, the recombinant viruses comprise one or more of the following: i) an introduced heterologous PPXY domain; ii) an increased number of PPXY domains; iii) a PPXY domain comprising a phosphomimetic amino acid at the Y position; and/or iv) a substituted amino acid in place of S41 in a viral Z protein, wherein the substituted amino acid is not a phosphomimetic and is not a substrate for a serine kinase. Thus, in certain embodiments the disclosure provides a modified arenavirus and populations thereof, wherein the modified arenaviruses comprise i) an introduced PPXY domain; ii) an increased number of PPXY domains; iii) a substituted amino acid in place of S41 in a viral Z protein that is not a substrate for a serine or tyrosine kinase, or a combination of i)-iii). In an embodiment the PPXY domain comprises a phosphomimetic replacement of the Y amino acid. In certain aspects the arenaviruses are Old World or New World arenaviruses. In a non-limiting example a modified Old World arenavirus with an introduced PPXY domain is provided. In another non-limiting embodiment a modified New World arenavirus comprising an increased number of PPXY domains is provided. In certain approaches a modified arenavirus is produced by cells that comprise a kinase inhibitor that is not made by the cells and which inhibits a kinase that can phosphorylate the Y amino acid of the PPXY domain, or by cells that have disrupted kinase gene expression, or cells that have a disrupted ESCRT system, or a combination thereof.

In one aspect, the disclosure comprises a pharmaceutical formulation that comprises modified arenaviruses. In another aspect modified arenaviruses and/or pharmaceutical formulations comprising them or arenaviruses made according to the disclosure are administered to a human or a non-human animal to stimulate an immune response against one or more proteins expressed by the arenavirus, and thus is expected to be suitable for stimulating an immune response that is fully or partially protective against arenavirus infection.

In another aspect the disclosure provides a method for producing a population of arenaviruses. The method generally comprises culturing cells that i) are infected with a wild type arenavirus, or ii) comprise one or more expression vectors encoding the arenavirus, wherein the cells are characterized by at least one of: a) comprising kinase inhibitor that is not produced by the cells; or b) a modification such that expression of a kinase capable of phosphorylating a tyrosine in a PPXY domain of the arenavirus is inhibited or eliminated, or c) a disrupted ESCRT pathway. As a consequence of practicing such methods, the arenaviruses produced fewer defective interfering arenavirus particles compared to infectious arenavirus particles, relative to a control. In an embodiment the control comprises a value determined from production of defective interfering arenavirus particles without a), or b), or c), or any combination of a), b) and c).

In other aspects the disclosure includes one or more expression vectors encoding modified arenaviruses, cell cultures comprising cells that contain the expression vectors, and/or cell cultures that produce arenaviruses, wherein the cell cultures can optionally include a kinase inhibitor.

BRIEF DESCRIPTION OF THE FIGURES

FIG. 1. The LCMV matrix protein PPXY late domain is reversibly phosphorylated. (A) Protein lysates from sucrosebanded LCMV strain Armstrong 53b particles were separated on polyacrylamide gels and stained with Coomassie brilliant blue. A gel slice containing the Z protein (indicated by the red box) was excised, subjected to in-gel tryptic and/or chymotryptic digestion, and extracted peptides were analyzed by mass spectrometry for the presence of phosphorylated peptides as described in the Materials and Methods. (B) Representative low energy collision-induced dissociation tandem mass spectra of a chymotryptic peptide harboring the indicated phosphotyrosine residue or the same peptide unphosphorylated. Both peptides were identified from virion-derived LCMV Z protein. The tandem mass spectra were collected in an Orbitrap (MS1)-linear ion trap (MS2) mass spectrometer. Y# denotes phosphotyrosine. The SEQUEST XCorr values, the precursor observed mass and the associated PPM are indicated. FIG. 8 shows the corresponding calculated and measured b- and y-type ions indicating identified fragment ion masses. (C) Depiction of the LCMV Z protein. G, glycine at position 2 that is myristoylated; RING, the central zinc-binding really interesting new gene (RING) domain; PPPY, LCMV's only known late domain that contains the Y88 site of phosphorylation. (D) Tyrosine 88 in the LCMV matrix protein is phosphorylated. HEK293T cells were transfected with an empty vector or a plasmid encoding LCMV Z (either WT or Y88F) with a C-terminal streptavidin binding peptide (SBP) tag. Following a 15 minute exposure to either water or the tyrosine phosphatase inhibitor, $H_2O_2$, Z was affinity purified from cell lysates using magnetic streptavidin beads and screened via western blot using antibodies specific for phosphotyrosine or the SBP tag. Results are representative of 3 independent experiments. (E) LCMV is phosphorylated in rodent cells. L929 cells were infected or not with a rLCMV that encodes a streptavidin binding peptide (SBP) fusion tag at the C terminus of Z. Two days later, cells were exposed to either water or the tyrosine phosphatase inhibitor, $H_2O_2$, for 15 minutes. SBP-tagged Z was then affinity purified from cell lysates using magnetic streptavidin beads and screened via western blot using antibodies specific for phosphotyrosine or the SBP tag. Results are representative of 3 independent experiments.

FIG. 2. The LCMV Z PPXY late domain is dispensable for the production of infectious LCMV particles. (A) Sequence alignment of arenavirus Z proteins reveals conservation of Y88 among most Old World, but not New World, arenaviruses. (B) Recombinant (r)LCMV containing substitutions at Z Y88 that either mimic constitutive phosphorylation (Y88E) or cannot be phosphorylated (Y88F and Y88A) were generated using reverse genetics as described in the Materials and Methods. Vero E6 cells were infected at an MOI of 0.01 and the quantity of infectious virus released at each of the indicated time points was determined via plaque assay. Data are presented as mean PFU±standard error of the mean (SEM) of 3 independent experiments. (C) Summary of two way analysis of variance (ANOVA) with Holm-Sidak's test for multiple comparisons of log-transformed data for virus growth curves in (B). (D) The area of plaques from rLCMV WT or Z Y88 mutants was measured using Image J. Data represent the mean±SEM of plaques analyzed from 16 wells from 6-well plates. Mean values were compared using the Kruskal-Wallis non-parametric test with Dunn's multiple comparisons test. (E) Mutation of the PPXY domain reduces Z budding function in a VLP assay while phosphorylation of this domain at Y88 does not further impact budding. A plasmid encoding LCMV Z WT, Z G2A, or the indicated Z Y88 mutants was transfected into HEK293T cells and 1 day later cells and VLP-containing supernatants were collected and screened via quantitative western blot for Z. The percent VLP release was calculated as the amount of Z protein found in the cell culture media relative to the amount in cells. Data are presented as mean release±SEM relative to WT Z from 3 independent experiments. A one way ANOVA with Holm-Sidak's test for multiple comparisons was used to compare the mean values. (C-E), n.s. (not significant), *$p<0.05$; $p<0.01$; *$p<0.001$; ****$p<0.0001$, as determined by the indicated statistical tests.

FIG. 5. The PPXY late domain drives the production of DI particles. (A-B) Development and validation of a plaque interference assay for the measurement of LCMV DI particle activity. In (A), a stock of rLCMV WT containing both standard infectious virus particles and DI particles was subjected to UV irradiation for 2 min to inactivate standard LCMV particles but spare DI particles. Serial 5-fold dilutions of this UV-treated virus preparation (UV-LCMV) were added to Vero E6 cells followed by a fixed amount of 50 PFU of the indicated challenge virus (rLCMV WT; Junin virus Candid 1, (JUNV C#1), or vesicular stomatitis virus (VSV)). Additional controls were wells that received i) media only, ii) serial 5-fold dilutions of the stock LCMV virus preparation before UV treatment (no UV LCMV), iii) serial 5-fold dilutions of the stock LCMV virus preparation following UV treatment (UV-LCMV), or iv) 50 PFU per well of standard LCMV, JUNV C#1, or VSV, as indicated. Following a 1 hr incubation at 37° C. to permit viral particle absorption, cells were overlaid with agarose and subsequently fixed and stained with crystal violet to visualize whether the UV-LCMV preparation impacted the ability of each virus to form plaques. The LCMV DI titer is expressed as plaque interfering units50 (PIU50) per mL of a given sample and was calculated as described in the Materials and Methods. In (B), rLCMV WT containing both standard and DI particles was subjected to the indicated filtration or not and then subjected to UV irradiation as described in (A). Serial 5-fold dilutions of each UV-LCMV preparation (filtered or not) were added to Vero E6 cells followed by a fixed amount of 50 PFU of rLCMV WT. As described in (A), the ability of these UV-LCMV preparations to interfere with the ability of standard LCMV to from plaques was measured via plaque assay and LCMV DI titers are reported as PIU50/mL. In (A-B), the graphical results represent the mean LCMV DI titer±SEM for 3 independent experiments and representative wells for each condition are shown directly below each graph. (C) LCMV DI particle production requires a functional PPXY domain. The rLCMV WT or Y88 mutants examined in FIG. 4 were subjected to the assay described in (A-B) to directly measure the DI particle titer present in each virus preparation. Briefly, each indicated rLCMV preparation was subjected to UV-irradiation to inactivate standard infectious LCMV particles while preserving DI particle activity. Serial 5-fold dilutions of each UV-treated sample were inoculated onto Vero E6 cells, followed by the addition of 50 PFU of standard LCMV. Following a 1 hr incubation at 37° C. to permit viral particle absorption, cells were overlaid with agarose and subsequently fixed and stained with crystal violet to visualize whether the various UV-treated rLCMV preparations impacted the ability of standard LCMV particles to form plaques. For each rLCMV, DI titer is reported as mean PIU50/mL±SEM for 3 independent experiments. (A-C) n.s. (not significant), *p<0.05; *p<0.001; **p<0.0001, determined by first substituting values of 19 PIU50/mL (just below the limit of detection value of 20 PIU50/mL) for samples that were below the limit of detection and then performing a one way ANOVA.

FIG. 8. Fragment ion tables from mass spectra and spectral counts of phosphorylated and unphosphorylated tryptic peptides. (A-B) For the indicated phosphorylated (A) and unphosphorylated (B) peptides, corresponding to the spectra shown in FIG. 1B, the calculated and measured (colored numbers) m/z values of the y- and b-type ions are shown. (C) The phosphorylated and unphosphorylated peptides detected from virion-derived LCMV Z in FIG. 1A are listed. Each MS/MS spectrum was manually examined and found to be correct by a comparison to spectra with the highest Xcorr values and by comparing predicted and observed fragment ions. (A and C) Y# indicates phosphorylated tyrosine.

FIG. 13. The LCMV matrix protein Z is phosphorylated at serine 41 (S41). (a) HEK-293T cells were transfected with a plasmid encoding streptavidin binding peptide (SBP)-tagged LCMV strain Armstrong Z or an empty vector. Two days later cells and virus-like particle (VLP)-containing supernatant were lysed and Z-SBP was affinity purified using streptavidin-coated magnetic beads. The purified Z-SBP was subjected to SDS-PAGE and detected by western blotting using an anti-SBP tag antibody or Coomassie stain. The presumptive monomeric Z bands from cells or VLPs were excised from the Coomassie stained gels (as indicated by the red boxes) and subjected to reduction, alkylation, and in-gel tryptic digestion prior to mass spectrometry analysis of extracted peptides. (b) A representative low energy collision-induced dissociation tandem mass spectrum with its corresponding fragment ion table from low energy collision-induced dissociation of a Z-derived tryptic peptide (FDS#LVR) containing the phosphorylated S41 where # denotes phosphorylation. The fragment ion table lists the predicted m/z values of the singly-charged b and y ions. Major measured b and y ions, as well as dominant losses of phosphoric acid are labeled. Phosphoric acid loss is a major signature in tandem mass spectra of phosphoserine/threonine-containing peptides. (c) Cartoon of the LCMV Z protein depicting the G2 myristoylation site, the central zinc-binding RING domain, and the C-terminal PPPY late domain. The S41 phosphorylation site and its flanking amino acids as well as the Y88 phosphorylation site are indicated. (d) Alignment of Old and New World arenavirus Z protein sequences shows that S41 is conserved with the Old World arenaviruses Dandenong and Ippy virus. The sequences in d are as follows:

Figure 3:
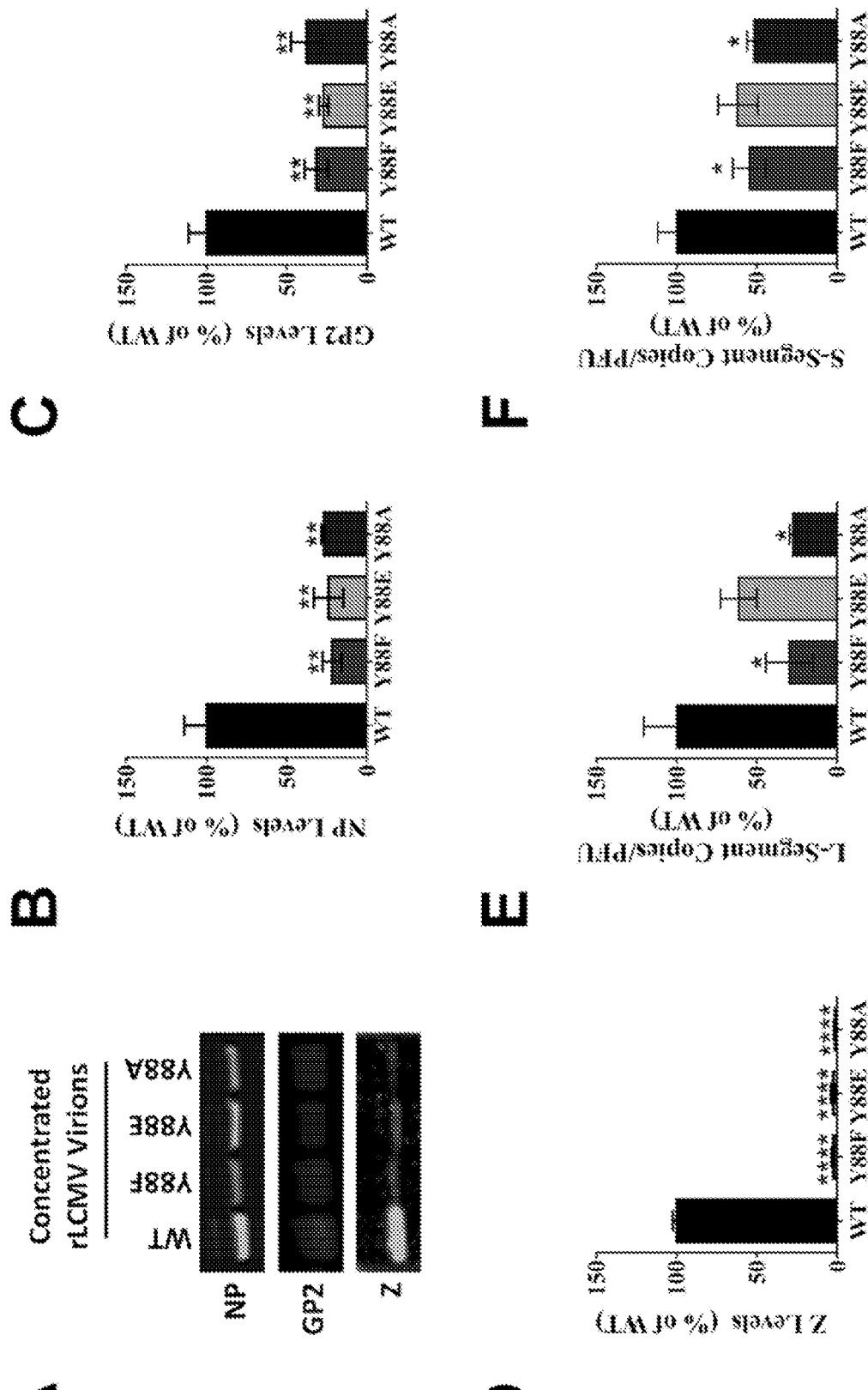
FIG. 3. PPXY late domain mutant viruses release substantially less viral structural proteins and genomes without a corresponding loss of infectious units. (A-E) An equal quantity of PFUs of rLCMV WT, Z Y88F, Z Y88E, or Z Y88A were concentrated via ultracentrifugation through sucrose and screened for viral NP (B), GP2 (C), or Z (D) via quantitative western blot or L segment vRNA (E) or S segment vRNA (F) via qRT-PCR. Representative western blots for NP, GP2, and Z are shown in (A). Data in (B-F) are representative of the mean±SEM relative to rLCMV WT from at least 3 independent experiments. (B-E) *$p<0.05$; $p<0.01$; **$p<0.0001$, determined using the one-way ANOVA with Holm-Sidak's test for multiple comparisons. Note that in panels B-F, the Y88 mutant viruses were not statistically different from one another.

```
WQKFDSLVRCH,      (SEQ ID NO: 7)
WFENKGLVECN,      (SEQ ID NO: 8)
WQRFDSLVRCH,      (SEQ ID NO: 9)
WFERKGLIKCQ,      (SEQ ID NO: 10)
WFERRGLVKCY,      (SEQ ID NO: 11)
WFERRSLVACN,      (SEQ ID NO: 12)
WKSKKALVKCY,      (SEQ ID NO: 13)
WFADTNLITCN,      (SEQ ID NO: 14)
WFADKNLIKCS,      (SEQ ID NO: 15)
WFANTNLIKCS.      (SEQ ID NO: 16)
```

FIG. 14. Phosphomimetic mutation of S41 significantly reduces the efficiency of infectious virus release and the ability of Z to form virus-like particles (VLPs). (a) Reverse genetics was used to generate rLCMV containing a non-phosphorylatable S41A mutation or a phosphomimetic S41D mutation. To determine whether infectious virus was recovered, both a standard plaque assay and an immunofocus assay (using an anti-nucleoprotein antibody (1.1.3)) were performed on Vero E6 cells. (b) The kinetics of infectious virus production were examined by growth curve analysis on Vero E6 cells (a multiplicity of infection (MOI) of 0.01 was used for each virus). Data represent the mean±SEM from 3 independent experiments. For statistical analysis, the data were first log-transformed then a two-way analysis of variance (ANOVA) with Holm-Sidak's test for multiple comparisons was performed. (c) The area of foci obtained from the immunofocus assay wells shown in (A) for each rLCMV strain was measured using Image J. Data represent the mean±SEM of foci from 8 wells for each virus. The Kruskal-Wallis non-parametric test with Dunn's multiple comparisons test was used to compare mean values. (d) The budding activity of WT or S41-mutant LCMV Z proteins was measured by a VLP release assay. The results shown represent the mean±SEM from 3 independent experiments. A one-way analysis of variance with the Holm-Sidak's test for multiple comparisons was used to compare the mean values. For the indicated statistical tests in (B-D), *, p<0.05, , p<0.01; **, and p<0.0001.

FIG. 15. The S41 phosphomotif regulates DI particle production. (a-f) Comparison of viral structural protein and genome content in preparations of rLCMV WT, S41A, or S41D virus. Vero E6 cells were infected with WT or S41-mutant rLCMV at a multiplicity of infection (MOI) of 0.0001 and clarified supernatants were collected 72 hours later. Equivalent FFUs of each rLCMV were then concentrated through a 20% sucrose cushion by ultracentrifugation. Viral protein content in these concentrated virus preparations was analyzed by quantitative western blotting. Representative western blots (a) as well as the quantity (mean±SEM) of NP (b), GP (c), or Z (d) contained in each rLCMV virus preparation are shown. The copies of LCMV genomic L segment (e) or S-segment (f) were determined by quantitative RT-PCR and then normalized to the infectious titer (FFU). (g-h) Measurement of standard infectious virus and DI particles produced by rLCMV WT, S41A, or S41D. Vero E6 cells were infected with the indicated viruses at an MOI of 0.0001 and 72 hours later supernatants were collected and clarified. The infectious titer of each virus was determined by focus forming assay (g) and the DI particle titer was assessed by plaque interference assay. PIU50/ml, plaque interfering units 50/ml For (b-h), the values represent the mean±SEM of protein quantities from 4 independent experiments and statistical analysis was performed by one-way ANOVA with Holm-Sidak's test for multiple comparisons for which *, p<0.05, , p<0.01; **, and p<0.0001. (i) Model of S41's impact on infectious virus and DI particle formation. WT virus containing the native S41 (Z WT) produces high levels of infectious and DI particles. Mutation of S41 to alanine (Z S41A) to prevent phosphorylation has little effect on infectious or DI particle production. Mutation of S41 to glutamic acid (Z S41D) to mimic the negative charge associated with phosphorylation of S41 results in decreased infectious virus and DI particle release. The S41D mutation disproportionately impacts DI formation over standard infectious virus.

Figure 16:
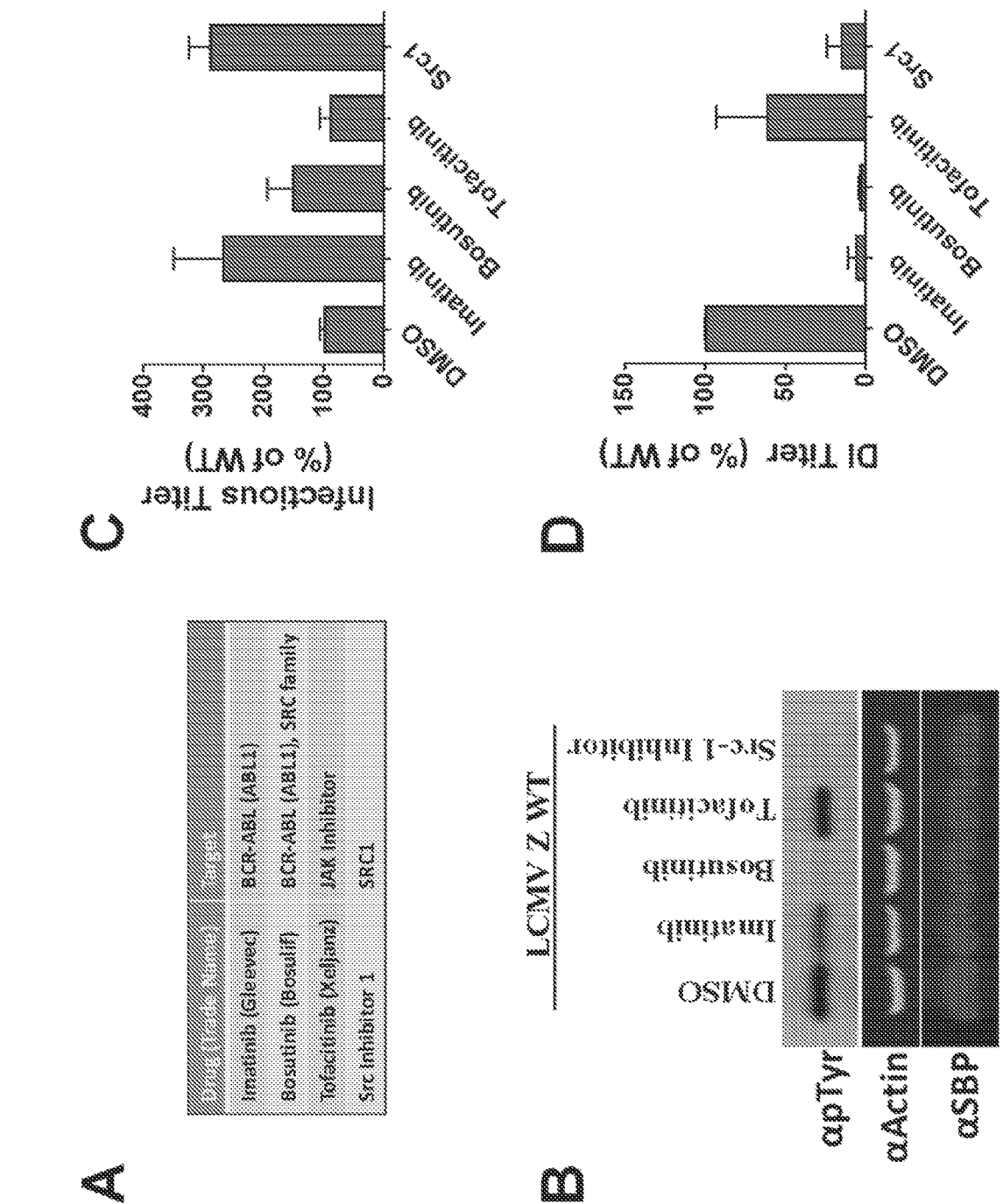

FIG. 16. Data demonstrating treatment of cell lines with tyrosine kinase inhibitors prevents phosphorylation of lymphocytic choriomeningitis virus (LCMV) Z and the production of LCMV DI particles while concomitantly increasing the release of infectious LCMV particles. (FIG. 16A) Table of selected tyrosine kinase inhibitors, their trade names (if applicable) and the cellular tyrosine kinase(s) they inhibit. Tofacitinib was included as a negative control, as it is not expected that JAK family tyrosine kinases phosphorylate PPXY motifs. (FIG. 16B) Cells expressing the LCMV Z protein were treated with tyrosine inhibitors and the level of phosphorylation was detected via western blot with a phosphotyrosine (pTyr)-specific antibody. Actin levels and Z protein levels (detected via the SBP affinity tag) were also detected by western blot. (FIG. 16C-FIG. 16D) Cells infected with LCMV were treated with tyrosine kinase inhibitors and the titers of infection virus (FIG. 16C) and DI particles (FIG. 16D) were detected via plaque assay and plaque interfering assay, respectively.

Figure 17:
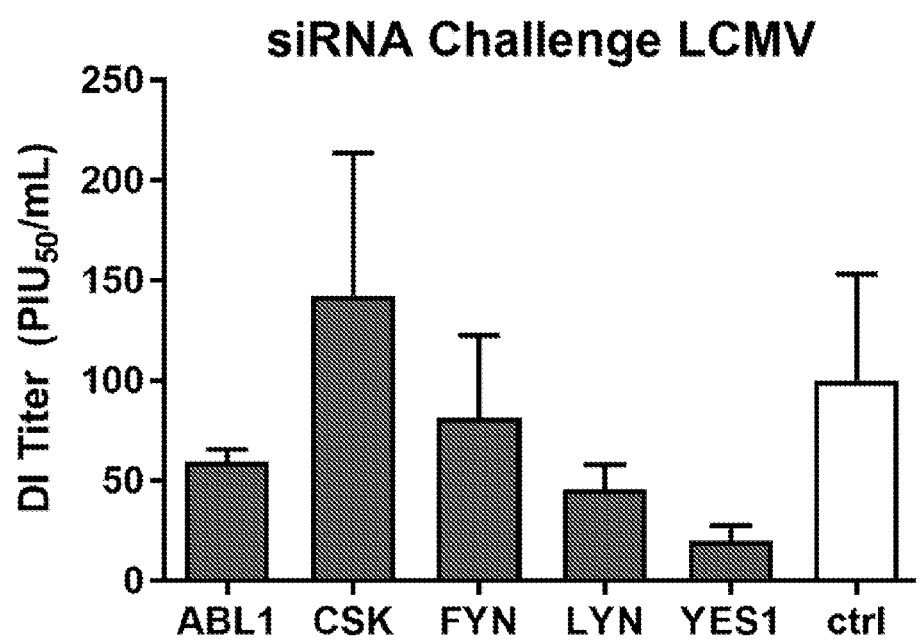

FIG. 17. Data showing siRNA-silencing of human kinases selectively reduces defective interfering particle production by lymphocytic choriomeningitis virus. siRNAs were used to selectively decrease the expression of tyrosine kinases in A549 cells which were subsequently infected with LCMV. DI particle titers were determined via plaque assay. FYN, LYN and YES1 are SRC family kinases. CSK is a tyrosine kinase that specifically inhibits the function of SRC family tyrosine kinases. An siRNA which does not target any human mRNA was used as a negative control (ctrl).

DESCRIPTION OF THE DISCLOSURE

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all polynucleotide and amino acid sequences described herein, and every polynucleotide sequence referred to herein includes its complementary DNA sequence, and also includes the RNA equivalents thereof to the extent an RNA sequence is not given. Every DNA and RNA sequence encoding polypeptides disclosed herein is encompassed by this disclosure, including but not limited to sequences encoding all recombinant proteins that comprise a segment of or a full protein, as described further below.

The present disclosure relates to modified arenaviruses, compositions comprising them, and methods of using them.

In more detail, Arenaviruses are a family of rodent-borne viruses with a worldwide distribution. These viruses typically establish persistent, asymptomatic infections in rodent reservoir species. In contrast, arenaviruses cause severe and often fatal diseases in humans. Several arenaviruses, including Lassa virus and Junin virus, cause hemorrhagic fever syndromes whereas infection with the prototypic arenavirus, lymphocytic choriomeningitis virus (LCMV), can lead to aseptic meningitis in immunocompetent individuals, high lethality in immunocompromised individuals, or severe birth defects in the developing fetus. U.S. Food and Drug Administration-approved vaccines do not exist for the prevention of arenavirus infection and effective antiviral therapies have been limited to the use of ribavirin for Lassa virus or immune plasma for Junin virus.

Arenaviruses are enveloped viruses with a single-stranded, bi-segmented RNA genome that encodes four proteins in an ambisense manner. The small (S) segment encodes the nucleoprotein (NP) and glycoprotein (GP) while the large (L) segment encodes the RNA-dependent RNA polymerase (L) and the matrix protein (Z). Arenaviruses enter cells via receptor-mediated endocytosis, undergo genomic replication and transcription in the cytoplasm, and assemble and bud new particles at the plasma membrane. The Z protein, which lines the luminal side of the viral membrane, is responsible for a number of functions in the virus life cycle, including driving the process of viral particle assembly and budding. Accordingly, Z can form virus-like particles (VLPs) in the absence of other viral proteins and is thought to be both necessary and sufficient for driving the budding process.

Z is believed to drive viral particle release by virtue of one or more encoded viral late domain(s) (P(S/T)AP, YXXL, and/or PPXY), which can recruit proteins from the cellular endosomal sorting complex required for transport (ESCRT) pathway. ESCRT machinery is required for most cellular membrane scission events that result in separation away from the cytosol including multivesicular body formation and cellular abscission. Many enveloped viruses are known to hijack cellular ESCRT machinery via their late domains to complete the final membrane scission step required for virions to bud from host membranes. As is known in the art, and without intending to be bound by any particular theory, it is considered that a viral late domain is comprised of any one of the foregoing tetrapeptide motifs, and functions to recruit cellular ESCRT proteins to complete the final scission step in viral budding. Cells comprising newly added or duplicated P(S/T)AP and YXXL sequences are encompassed in this disclosure.

Viruses from diverse families, including arenaviruses, produce defective interfering (DI) particles in addition to standard, infectious virus during the normal course of infection. DI particles are largely similar to standard virus particles in their appearance and viral protein content but cannot self-replicate, and interfere with the production of homologous standard virus. In many cases, the primary difference between DI particles and standard virus is thought to be the presence of deletions in the viral genome. With regard to LCMV, small deletions in the terminal untranslated regions of genomic and antigenomic RNAs have been observed, but it is not known whether these RNAs have interfering properties or are selectively incorporated in DI particles. The interfering activity of arenavirus DI particles can be blocked by neutralizing antibodies but is maintained even after treatment with ultra-violet (UV) radiation, unlike standard particles, which are highly susceptible to both treatments. Arenaviruses generate high levels of DI particles both in cell culture and in host rodents. It has long been postulated that arenavirus DIs are an important factor in the establishment of persistent infection but a causal link between arenavirus DI particles and persistence has yet to be firmly established.

It is demonstrated in the present disclosure that neither the PPXY late domain encoded within the LCMV Z protein nor a functional ESCRT pathway is absolutely required for the generation of standard infectious virus particles. In contrast, DI particle release requires the PPXY late domain and is dependent on the ESCRT pathway. Additionally, the terminal tyrosine in the PPXY motif is reversibly phosphorylated and data presented herein indicate that this posttranslational modification affects DI particle formation. (The terminal tyrosine in the PPXY sequence is amino acid number 88 in the LCMV Z protein sequence. The WT LCMV Z gene is provided under NCBI gene identifier number AY847351 while the translated amino acid sequence for the WT Z gene is provided under Protein Locus number AAX49343. These sequences are incorporated herein by reference as they are provided under their respective identifier numbers as of the date of filing of this application or patent.) Thus a new role for the PPXY late domain and mechanism for its regulation are encompassed within this disclosure. The present disclosure also demonstrates that LCMV Z protein, which drives viral budding, is phosphorylated at serine 41. A recombinant (r)LCMV bearing a phosphomimetic mutation (S41D) was impaired in infectious and defective interfering (DI) particle release while a nonphosphorylatable mutant (S41A) was not. The S41D mutant was thus disproportionately impaired in its ability to release DI particles relative to infectious particles. Accordingly, and without intending to be bound by any particular theory, it is considered that phosphorylation at Y88 of LCMV Z increases DI particle production, whereas phosphorylation of LCMV Z S41 represses it. Based at least in part on these findings, the present disclosure comprises recombinant/modified viruses, expression vectors encoding them, compositions comprising them, and methods of making and using them. In non-limiting examples, the recombinant viruses comprise one or more of the following: i) an introduced heterologous PPXY domain; ii) an increased number of PPXY domains; iii) a PPXY domain comprising a phosphomimetic amino acid at the Y position; and/or iv) a substituted amino acid in place of S41 in a viral Z protein, wherein the substituted amino acid is not a phosphomimetic and is not a substrate for a serine kinase. Each of i)-iv), and any combination of them, can be achieved—given the benefit of this disclosure—using standard molecular biology techniques.

In general, and without intending to be constrained by any particular theory, it is considered that modifying an arenavirus according to i)-iv) and combinations thereof will skew viral replication towards the production of more DI particles, relative to an arenavirus that is not modified with any of the features illustrated in i)-iv). Thus, compared to wild type virus, or a suitable reference virus that does not have any of modifications i)-iv), the presently provided modified viruses may produce an increased proportion of DI particles relative to infectious particles. As will be recognized by those skilled in the art when given the benefit of the present disclosure, increasing the proportion of DI particle production, relative to infectious particles, can facilitate production of compositions that are suitable for use in vaccination as viruses that produce more DI particles in relation to infectious particles can be considered to be attenuated compared to wild type virus.

DI particles can enter host cells, but cannot propagate on their own. Arenavirus DI particles can block the propagation of infectious virus with 1 hit kinetics meaning that a single DI particle, if taken into a permissive host cell, can block the ability of an infectious virion that enters the same cell from propagating. It is not fully understood how arenavirus DI particles interfere with infectious virus propagation, but it may be similar to other virus families whereby the DI particle genome, which is defective for replication and/or transcription, recruits the replication machinery from the infectious particle. By sequestering the replication machinery on the defective genome, replication and transcription of the wild type genome from the infectious virus is blocked. It is also possible that the DI property could be caused by Z interfering with the polymerase. Irrespective of precise mechanism, DI particles are believed to block n the ability of infectious viruses to infect new host cells, which results in attenuation of the virus, and in particular its ability to spread efficiently in a new host before the host immune system will clear the virus. Thus, in certain aspects the disclosure comprises producing an increased amount of "functional" DI particles, meaning arenavirus particles that can enter a target cell, thereby delivering the DI particle contents to the cytoplasm of the target cell in a way that is similar to the delivery of infectious particle genomes to target cells during arenavirus infections. As such, DI particles of this disclosure are membrane-enveloped, and are formed by budding from host "producer" cells as described further herein. The presence and amount of DI particles can be determined using any suitable approach. In certain embodiments a plaque interference assay (also known as a plaque reduction assay), or a focus interfering assay, are used.

The disclosure includes polynucleotides encoding the modified arenaviruses of this disclosure. The polynucleotides can be DNA or mRNA encoding the viruses, or arenaviral genome RNA. DNA or RNA can be introduced directly into cells. In certain approaches expression vectors, such as plasmids, are used. A variety of suitable expression vectors known in the art can be adapted to produce the modified arenavirus particles of this disclosure. In general, the expression vector comprises sequences that are operatively linked with the sequences encoding the arenaviral proteins. A particular polynucleotide sequence is operatively-linked when it is placed in a functional relationship with another polynucleotide sequence. For instance, a promoter is operatively-linked to a coding sequence if the promoter affects transcription or expression of the coding sequence. Generally, operatively-linked means that the linked sequences are contiguous and, where necessary to join two protein coding regions, both contiguous and in reading frame. However, it is well known that certain genetic elements, such as enhancers, may be operatively-linked even at a distance, i.e., even if not contiguous, and may even be provided in trans. Promoters present in expression vectors that are used in the present disclosure may be endogenous or heterologous to the host cells, and may be constitutive or inducible, and may be mammalian promoters, including but not necessarily limited to human promoters. Expression vectors can also include other elements that are known to those skilled in the art for propagation, such as transcription and translational initiation regulatory sequences operatively-linked to the polypeptide encoding segment. Suitable expression vectors may include, for example, an origin of replication or autonomously replicating sequence (ARS) and expression control sequences, an enhancer and other regulatory and/or functional elements, such as ribosome-binding sites, RNA splice sites, polyadenylation sites, transcriptional terminator sequences, and mRNA stabilizing sequences, as well as a wide variety of selectable markers.

In certain aspects the disclosure thus includes introducing into cells one, two, three or four distinct polynucleotides (including but not necessarily limited to distinct polynucleotides that may be maintained as episomal elements), wherein the polynucleotides encode arenavirus NP, GP, L and Z proteins. In embodiments, one or more polynucleotides can encode the S and/or L RNA segments of an arenavirus. In alternative embodiments, fewer than four distinct polynucleotides can be used. Thus, the four viral components can be encoded by 4, 3, 2, or 1 polynucleotide. In certain aspects, cells can be engineered to stably express any of or more of the viral components. Such stable expression can be achieved using a variety of approaches known to those skilled in the art given the benefit of the present disclosure, and include but are not limited to chromosomally integrated polynucleotides, or by using selection agents to maintain one or more episomal elements that encode one or more of the four viral components. Cell lines encoding 1, 2, 3 or 4 of the of the viral components are therefore included in the scope of this disclosure, as are methods of making and using such cells and cell lines to produce arenaviral preparations.

Methods of making the modified arenavirus particles are included and generally comprise introducing one or more polynucleotides encoding arenaviral genome segments and arenaviral proteins as described above into cells, and allowing expression of the polynucleotides such that arenaviral particles are formed, wherein the arenaviral particles comprise an increased amount of DI particles relative to a control. In certain aspects the DI particles can comprise a large proportion, in relation to infectious particles, of the total arenaviral particles that are produced. The quantity of infectious and DI particles produced by each particular recombinant virus can be determined with standard plaque and/or focus assays for infectious particles and plaque interference assay for DI particles.

The expression vectors can be introduced into host cells for producing viral particles by any method known in the art. These methods vary depending upon the type of cellular host, and include but are not limited to transfection employing cationic liposomes, electroporation, calcium chloride, rubidium chloride, calcium phosphate, DEAE-dextran, other substances as will be apparent to the skilled artisan. Host cells designed to propagate viral particles can be referred to as "producer cells." In certain embodiments the producer cells are mammalian cells.

As discussed above, the disclosure includes recombinant viruses which comprise one or more of the following: i) an introduced heterologous PPXY domain; ii) an increased number of PPXY domains; iii) a PPXY domain comprising a phosphomimetic amino acid at the Y position; and/or iv) a substituted amino acid in place of S41 in a viral Z protein, wherein the substituted amino acid is not a phosphomimetic and is not a substrate for a serine kinase.

For i) an introduced heterologous PPXY domain, the disclosure includes inserting a sequence encoding at least one PPXY domain into an arenavirus genome that does not comprise an endogenous PPXY domain. Without intending to be bound by any particular theory, it is considered that introducing such a domain into an arenavirus that does not already contain a PPXY domain will result in the increased production of DI particles by the modified arenavirus. For example, as shown in Table A below, several New World arenavirus, including but not necessarily limited to Junin Virus, Guanarito Virus, Machupo Virus, and Sabia Virus, do not include a PPXY domain. Accordingly, introducing at least one PPXY domain into any such virus is expected to result in the modified virus producing more DI particles, which will attenuate this virus via production of increased DI particles, and facilitate vaccine production against infection by the respective unmodified viruses.

TABLE 1

Sequence Alignment

| Virus (strain) | Peptide Sequence |
|---|---|
| Old World | |
| LCMV-Armstrong | PPPYEE |
| LCMV-WE | PPPYEE |
| Lassa Virus-Josiah | PPPYSP |
| Dandenong virus | PPPYEE |
| Mobala Virus | PPPYSP |
| Mopeia Virus-Mozambique | PPPYTP |
| Ippy Virus | PPPYSP |
| Lujo Virus | PP- |
| New World | |
| Junin Virus | PPP- |
| Guanarito Virus | PPE- |
| Machupo Virus | PPP- |
| Sabiá Virus | PPPED- |

The amino acid sequences of the proteins described above are presented under the following GenBank accession numbers: AAX49343 (LCMV Armstrong), AAD03395.1

(LCMV WE), NP_694871.1 (Lassa Virus Josiah), ABY20731 (Dandenong virus), ABC71138.1 (Mobala virus), ABC71136.1 (Mopeia Virus Mozambique), ABC71142.1 (Ippy virus), YP_002929492 (Lujo virus), NP_899216 (Junin virus), NP_899220 (Guanarito virus), NP_899214 (Machupo virus), ABY59837 (Sabiá virus). Each of the sequences associated with these identification numbers are incorporated herein as they exist in the database as of the filing date of this application or patent. Sequence is Table 1 are as follows:

```
PPPYEE -;           SEQ ID NO: 2

PPPYSP -;           SEQ ID NO: 3

PPPYTP -;           SEQ ID NO: 4

PPPED -.            SEQ ID NO: 5
```

For the non-limiting Examples described below, LCMV strain Armstrong 53 (a Lymphocytic choriomeningitis mammarenavirus, discussed above in connection with AAX49343.1), was used. Its Z binding protein comprises the sequence:

```
                                          (SEQ ID NO: 1)
MGQGKSREEKGTNSTNRAEILPDTTYLGPLSCKSCWQKFDSLVRCHDHYL

CRHCLNLLLSVSDRCPLCKYPLPTRLKISTAPSSPPPYEE.
```

Other viral Z protein sequences that are known in the art and can be used in embodiments of this disclosure include but are not limited to the following, which are each preceded by accession numbers and the particular virus names:

AAD03395.1 Z protein [Lymphocytic choriomeningitis mammarenavirus]

```
                                          (SEQ ID NO: 17)
MGQGKSKEERDTSNTGRAELLPDTTYLGPLNCKSCWQKFDSLVRCHDHY

LCRHCLNLLLLSVSDRCPLCKYPLPTKLKVSTVPSSLPPYEE
```

NP_694871.1 Z protein [Lassa mammarenavirus]

```
                                          (SEQ ID NO: 18)
MGNKQAKAPESKDSPRASLIPDATHLGPQFCKSCWFENKGLVECNNHYL

CLNCLTLLLSVSNRCPICKMPLPTKLRPSAAPTAPPTGAADSIRPPPYSP
```

ABY20731.1 Z protein [Dandenong virus]

```
                                          (SEQ ID NO: 19)
MGQAKSKETKLSKKEDRAEVLPDATYLGPLNCKSCWQRFDSLVRCHDH

YLCRQCLNLLLTVSDRCPLCKHPLPTKLRVSTAPSSPPPYEE
```

ABC71138.1 Z protein [Mobala mammarenavirus]

```
                                          (SEQ ID NO: 20)
MGQKPSKPKAPPTTYESPRSSLTPDATGFGPEFCKSCWFERKGLIKCQNH

YLCMTCLTLLLTVSNRCPVCKYPLPTKLRLEKSPTAPPPEATNPPPYSP
```

ABC71136.1 Z protein [Mopeia mammarenavirus]

```
                                          (SEQ ID NO: 21)
MGKSQSKSSPHNKPPEPEAPRHPVIPDARGTGPEFCKSCWFERRGLVKCY

DHYLCLNCLTLLHTVSDRCPICKHTLPLKLELQTQPTAPPEHPPNQQPPP

YTP
```

ABC71142.1 Z protein [Ippy mammarenavirus]

```
                                          (SEQ ID NO: 22)
MGQNQSRDKQKAIQNQPKDTGNRADIIPDATGMGPEFCKSCWFERRSLV

ACNNHYLCMNCLTLLLSVSERCPICKLPLPQKLKLTSSPSAPPSPSPPPY

SP
```

YP_002929492.1 multifunctional matrix-like protein [Lujo mammarenavirus]

```
                                          (SEQ ID NO: 23)
MGQRHSSGSGQPNPKPSDSDHEARRSELHSDASHLGPLNCKSCWKSKKA

LVKCYDHYLCLNCLSLLMGITPRCPFCYRELPKNLDLAEAPSAPPL
```

NP_899216.1 Z protein [Junin mammarenavirus]

```
                                          (SEQ ID NO: 24)
MGNCNGASKSNQPDSSRATQPAAEFRRVAHSSLYGRYNCKCCWFADTN

LITCNDHYLCLRCHQGMLRNSDLCNICWKPLPTTITVPVEPTAPPP
```

NP_899220.1 Z protein [Guanarito mammarenavirus]

```
                                          (SEQ ID NO: 25)
MGNSKSKSNPSSSSESQKGAPTVTEFRRTAIHSLYGRYNCKCCWFADKNL

IKCSDHYLCLRCLNVMLKNSDLCNICWEQLPTCITVPEEPSAPPE
```

NP_899214.1 Z protein [Machupo mammarenavirus]

```
                                          (SEQ ID NO: 26)
MGNCNKPPKRPPNTQTSSNQPSAEFRRTAPPSLYGRYNCKCCWFADTNLI

TCNDHYLCLRCHQTMLRNSELCHICWKPLPTSITVPVEPSAPPP
```

ABY59837.1 Z protein [Sabia mammarenavirus]

```
                                          (SEQ ID NO: 27)
MGNSKSKSKLSANQYEQQTVNSTKQVAILKRQAEPSLYGRHNCRCCWFA

NTNLIKCSDHYICLKCLNIMLGKSSFCDICGEELPTSIVVPIEPSAPPPE

D
```

With respect to ii)—engineering an increased number of PPXY domains, this embodiment can be utilized in arenaviruses which already contain a PPXY domain, or in arenaviruses that do not. It will be recognized that introducing any PPXY domain into an arenavirus falls within this category. For those arenaviruses that contain an endogenous PPXY domain, and without intending to be being constrained by any particular concept, it is expected that providing additional PPXY late domains will enable an increase in production of DI particles (relative to a suitable control), due to having at least an increase in viral particles which have a phosphorylated PPXY site, and/or by having more than one PPXY site phosphorylated in any particular Z protein. In certain embodiments the disclosure includes introducing 1, 2, 3, 4, 5, or more PPXY sites. In certain implementations the PPXY sites are introduced at or within 10 amino acids of the C-terminus of the Z protein. In certain embodiments, at least one additional PPXY sequence is added to the Z protein of an Old World virus.

With respect to iii)—a PPXY domain comprising a phosphomimetic amino acid at the Y position, without intending to be bound by any particular theory, this embodiment may be used as an alternative to, or in combination with i), ii) and iv). As discussed above, the Y position is Z protein amino acid number 88. Using standard approaches the Y can be altered to mimic the phosphorylated site by replacing the Y with any amino acid or other moiety that mimics phosphotyrosine. Non limiting embodiments include replacing Y88 with glutamate or aspartic acid to mimic the negative charge of the phosphate. The disclosure includes modifications comprising combinations of introducing one or more PPXY sites and PPXY where Y is replaced with a phosphomimetic amino acid.

With respect to iv)—a substituted amino acid in place of S41 in a viral Z protein, wherein the substituted amino acid is not a phosphomimetic and is not a substrate for a serine kinase—it is considered that any amino acid other than aspartic acid or glutamic acid can be used to replace the serine at position 41 in the Z protein.

Introducing one or more PPXY sites into an arenavirus according to this disclosure can be achieved using standard molecular biology methods and reagents, given the benefit of this disclosure. Examples of modifying PPXY sites are provided below via making mutations to the PPXY site, such as a phenylalanine mutant (Y88F) that cannot be phosphorylated. It is considered that any amino acid can be present in the X position in the PPXY site. Non-limiting examples of amino acids present in the X position of specific viruses are given in Table 2.

TABLE 2

List of viruses that contain a PPXY late domain and the identity of the amino acid at the third (X) position in the motif.

| Virus Family | Virus | Amino Acid "X" in PPXY |
| --- | --- | --- |
| Arenavirus | Lymphocytic Choriomeningitis Virus (Armstrong 53b) | P |
| | Lassa Virus | P |
| | Dandenong Virus | P |
| | Mobala Virus | P |
| | Mopeia Virus | P |
| | Ippy Virus | P |
| Rhabdovirus | Rabies Virus | E |
| | Vesicular Stomatitis Virus | P |
| Filovirus | Ebola Virus | E |
| | Marburg Virus | P |
| Retrovirus | Moloney Murine Leukemia Virus | P |
| | Mason-Pfizer Monkey Virus | P |
| | Human T Cell Leukemia Virus | P |
| | Rous Sarcoma Virus | P |
| | Bovine Leukemia Virus | P |
| | Koala retrovirus | P |
| Reovirus | Bluetongue virus | R |
| Hepadnavirus | Hepatitis B Virus | A |

Modified arenaviral particles produced recombinantly according to this disclosure can be isolated from cell culture media and/or supernatants, and separated to provide viral particle preparations. Thus, cells and cell cultures that harbor polynucleotides encoding the modified viruses are included, as are isolated and/or purified modified viral preparations. The particles, i.e., modified arenaviral particles, can be purified to any desired degree of purity using standard approaches, such as density gradient separation.

In embodiments the disclosure includes reduction or elimination of endogenous kinase activity (e.g. through use of kinase inhibitors, siRNAs directed against a particular kinase, and/or the use of cells lacking a particular kinase or encoding nonfunctional forms of a kinase) to inhibit the formation of DI particles and/or enhance vaccine production (e.g. production of infectious live attenuated viral vaccine particles). In general this approach can be extended to any virus that relies at least in part on phosphorylation to enhance production of DI particles independently of standard infectious particles. Without intending to be bound by any particular theory, it is considered that inhibition of a kinase (or otherwise reducing kinase activity and/or expression), wherein the kinase activity promotes the formation of DI particles, will favor the production of wild type infectious virus particles (the absence of DI particle production will leave more cells in the culture capable of supporting a production infection with standard infectious virus particles). The term "wild type" with respect to viruses and DI particle formation as used herein means a virus that has not been engineered such that it has an initially introduced PPXY motif (such as a New World virus that does not encode a PPXY motif), and it has not been engineered so that an endogenous PPXY motif has been altered (i.e., has not been changed to include a phosphomimetic) or duplicated. Thus, use of producer cells that are infected with an arenavirus or another virus that encodes a protein with a kinase-recognition domain that promotes DI particle formation independent of standard infectious virus, wherein the endogenous producer cell kinase activity is reduced or eliminated, is expected to improve production of viral particles due to reduced DI particle generation during culturing, which provides more cells for productive infection with standard infectious particles. In addition to wild type viruses, this approach is extended to viruses that are engineered to include either an initial introduced PPXY domain (meaning prior to modification the viral genome did not encode a PPXY domain), or to include more than one copy of a PPXY domain that is not part of the wild type virus. It is considered that such engineered viruses, when generated in producer cells that have reduced kinase activity, will yield fewer DI particles than would be expected in the absence of reduction of the kinase activity. Those skilled in the art will recognize that in general, the kinases for which activity is reduced according to embodiments of this disclosure are tyrosine kinases, and thus phosphorylation of Y88 of LCMV Z, or its equivalent in other viruses, is reduced. In embodiments the disclosure can exclude use of inhibitors that are specific or selective for serine kinases, such that inhibition of phosphorylation of LCMV Z S41 is not specifically or selectively limited.

Culturing producer cells that have inhibited kinase activity as described herein will enhance production of standard infectious viral particles due to the accompanying reduction in DI particle production. In the case of engineered viruses that have been modified to include one, or duplicate copies of a PPXY domain, once the engineered viruses are isolated from the producer cell culture, they will also be separated from the kinase inhibitor, and/or an intracellular producer cell environment that lacks or has reduced kinase activity. This is accordingly akin to a derepression of DI particle formation, and permits the presence of the introduced or endogenous PPXY domain to function to enhance the DI particle formation when liberated from the kinase-repressed environment, such as when the engineered viruses infect cells in which kinase activity is not inhibited. Thus, the disclosure provides for making vaccine stocks that were produced with reduced DI generation, but are fully capable of producing DI particles when used as vaccines, and as such constitute attenuated vaccine preparations. It will be recognized from this disclosure that this approach is therefore suitable for producing higher amounts of attenuated (and wild type) viruses than has previously been available, the attenuated viruses being capable of enhanced formation of DI particles only when exposed to suitable kinase activity. Accordingly, in one embodiment the disclosure comprises a method of culturing producer cells infected with an arenavirus (or other types of virus(es) that rely on phosphorylation for DI particle production independently of standard infectious virus particles) in the producer cells wherein kinase activity is reduced or eliminated, and further comprises separating the arenavirus particles from the cell culture, and making pharmaceutical formulations comprising the arenavirus particles separated from the culture. In embodiments the disclosure comprises re-infecting cells with particles separated from the cell culture. In embodiments the disclosure comprises introducing a pharmaceutical formulation comprising attenuated viral particles (i.e., engineered viruses that produce more DI particles relative to a wild type or other suitable control in the absence of a kinase inhibitor) of this disclosure to an individual in need thereof. The disclosure includes the cell cultures and cells infected with wild type and engineered viruses, including the cell culture medium that also comprise a kinase inhibitor.

In embodiments the disclosure includes viruses, cells, cell cultures, and methods of making and using them, wherein the cells produce an altered amount of DI particles and/or non-defective particles relative to a control. The control can be any suitable control, such that an amount of DI particles produced by an unmodified virus of the same type or strain, or a value or other reference derived therefrom. Controls can also comprise virulent and avirulent strains of the same virus, and other values that will be apparent to those skilled in the art given the benefit of this disclosure. Controls can also be values obtained from virus product by producer cells wherein, as described herein, the cells do not have repressed or inhibited kinase activity, and/or do not have disrupted ESCRT activity. Controls can also comprise an amount of viral particles released from cells, and/or a percent of VLP release. Values obtained from plaque assays and plaque inhibition assays can also be used as controls, as can measurements obtained from analysis of viral budding.

As discussed above, in certain approaches the disclosure includes exposing producer cells to a suitable kinase inhibitor and/or an agent that reduces kinase expression. Suitable kinase inhibitors can be small molecule compounds, or biologic agents. Suitable kinase inhibitors are known in the art and are commercially available. For use in embodiments of the disclosure the kinase inhibitor need not necessarily have a regulatory approval for use as a human agent because embodiments of the disclosure do not include administration of the kinase inhibitor to a human, but rather only as an agent used during viral particle generation. The kinase inhibitor can be removed from the viral particle preparation for use in pharmaceutical formulations. A list of kinase inhibitors can be found, for example, at www.brimr.org/PKI/PKIs.htm, from which the list of kinase inhibitors and their structures are incorporated herein by reference as they are on the filing date of this application or patent. Particular and non-limiting kinase inhibitors that can be used with embodiments of this disclosure not limited to small molecules and biologic agents. In certain approaches the kinase inhibitor is Imatinib, sold under the trade name GLEEVEC®, or is Dasatinib, or Erlotinib, or Nilotinib, or Sorafenib, or Bonsutinib, or Tofacitinib, or Src Inhibitor 1 (SRC1). In non-limiting demonstrations, FIG. 16 presents data showing that tyrosine kinase inhibitors prevents phosphorylation of LCMV Z protein, which is correlated with a decrease in production of LCMV DI particles and an increase in release of infectious LCMV particles.

In another approach one or more agents that can reduce kinase expression in producer cells are employed. Such agents include but are not necessarily limited to those that can function using polynucleotide mediated downregulation of protein expression. In general, such approaches include RNAi-mediated reduction in kinase mRNA. RNAi-based inhibition can be achieved using any suitable RNA polynucleotide that is targeted to the kinase mRNA. In embodiments, a single stranded or double stranded RNA, wherein at least one strand is complementary to the kinase-encoding mRNA, can be introduced into the cell to promote RNAi-based degradation of kinase-encoding mRNA. In another embodiment, microRNA (miRNA) targeted to the kinase-encoding mRNA can be used. In another embodiment, a ribozyme that can specifically cleave kinase-encoding mRNA can be used. In yet another embodiment, small interfering RNA (siRNA) can be used. siRNA (or ribozymes) can be introduced directly, for example, as a double stranded siRNA complex, or by using a modified expression vector, such as a lentiviral vector, to produce an shRNA. As is known in the art, shRNAs adopt a typical hairpin secondary structure that contains a paired sense and antisense portion, and a short loop sequence between the paired sense and antisense portions. shRNA is delivered to the cytoplasm where it is processed by DICER into siRNAs. siRNA is recognized by RNA-induced silencing complex (RISC), and once incorporated into RISC, siRNAs facilitate cleavage and degradation of targeted mRNA. In embodiments, an shRNA polynucleotide used to suppress kinase-encoding mRNA and protein expression can comprise or consist of between 45-100 nucleotides, inclusive, and including all integers between 45 and 100. The portion of the shRNA that is complementary to the kinase-encoding mRNA can be from 21-29 nucleotides, inclusive, and including all integers between 21 and 29. In a non-limiting demonstration FIG. 17 demonstrates that siRNA-silencing of human kinases selectively reduced DI particle production in a representative lymphocytic choriomeningitis virus.

For delivering siRNA via shRNA, modified lentiviral vectors can be made and used according to standard techniques, given the benefit of the present disclosure. Further, lentiviral vectors expressing shRNAs targeted to many human mRNAs are commercially available. Additionally, custom siRNAs or shRNA can be obtained from commercially available sources for transient transfection resulting in temporary reduction kinase-encoding mRNA levels. Alternatively, suitable lentiviral constructs are capable of stably and permanently infecting producer cells, such as by integrating into a chromosome.

In another aspect, the disclosure includes disrupting the kinase gene in producer cells such that kinase-encoding mRNA and the kinase protein are not expressed. In one embodiment, the kinase gene can be disrupted by targeted mutagenesis. In embodiments, targeted mutagenesis can be achieved by, for example, targeting a CRISPR (clustered regularly interspaced short palindromic repeats) site in the kinase gene. So-called CRISPR systems designed for targeting specific genomic sequences are known in the art and can be adapted to disrupt the target gene for making modified cells encompassed by this disclosure. In general, the CRIPSR system includes one or more expression vectors encoding at least a targeting RNA and a polynucleotide sequence encoding a CRSPR-associated nuclease, such as Cas9, but other Cas nucleases can be used. CRISPR systems for targeted disruption of mammalian chromosomal sequences are commercially available and can be adapted for use in embodiments of this disclosure.

In embodiments, a targeting RNA encoded by the CRISPR system can be a CRISPR RNA (crRNA) or a guide RNA, such as sgRNA. The sequence of the targeting RNA has a segment that is the same as or complementarity to any CRISPR site in the target gene. In this regard, the target sequence comprises a specific sequence on its 3' end referred to as a protospacer adjacent motif or "PAM". In an embodiment a CRISPR Type II system is used, and the target sequences therefore conform to the well-known N12-20NGG motif, wherein the NGG is the PAM sequence. Thus, in embodiments, a target RNA will comprise or consist of a segment that is from 12-20 nucleotides in length which is the same as or complementary to a DNA target sequence (a spacer) in the target gene. The 12-20 nucleotides directed to the spacer sequence will be present in the targeting RNA, regardless of whether the targeting RNA is a crRNA or a guide RNA. In embodiments, a separate trans-activating crRNA (tracrRNA) can be used to assist in maturation of a crRNA targeted to a kinase gene. Introduction of a CRISPR system into producer cells will result in binding of a targeting RNA/Cas9 complex to the target kinase sequence so that the Cas9 can cut both strands of DNA causing a double strand break. The double stranded break can be repaired by non-homologous end joining DNA repair, or by a homology directed repair pathway, which will result in either insertions or deletions at the break site, or by using a repair template to introduce mutations, respectively. Double-stranded breaks can also be introduced by expressing Transcription activator-like effector nucleases (TALENs) in the producer cells. TALENs are artificial restriction enzymes generated by fusing a TAL effector DNA binding domain to a DNA cleavage domain and are known in the art and can be adapted for use in embodiments of this disclosure. In yet another approach, zinc-finger nucleases (ZFNs) can be expressed in the producer cells to target the kinase gene. ZFNs are artificial restriction enzymes produced by fusing a zinc finger DNA-binding domain to a DNA-cleavage domain. ZF domains can be designed to target the kinase gene DNA sequences where the zinc-finger nucleases cleave the sequence, thereby disrupting the gene. In embodiments the producer cells comprise a knock-out of a tyrosine kinase gene, which may be a homozygous or heterozygous knock-out.

In certain approaches the disclosure relates to use of producer cells that comprise a disrupted ESCRT system. The ESCRT system can be disrupted using any suitable technique or approach. In embodiments, the ESCRT system is disrupted using polynucleotide/enzyme based approaches as discussed above in connection with targeting a kinase gene. In embodiments, the producer cells produce a dominant negative ESCRT protein (e.g. the VPS4 EQ dominant negative mutant that, when expressed, inhibits recycling of ESCRT machinery within cells) which limits production of DI particles relative to cells that do not have a disrupted ESCRT system.

In certain aspects the disclosure includes a pharmaceutical formulation comprising modified arenaviruses as described herein. The form of pharmaceutical preparation is not particularly limited, but generally comprises modified arenaviruses and at least one inactive ingredient. In certain embodiments suitable pharmaceutical compositions can be prepared by mixing modified arenaviruses with a pharmaceutically-acceptable carrier, diluent or excipient, and suitable such components are well known in the art. Some examples of such carriers, diluents and excipients can be found in: Remington: The Science and Practice of Pharmacy (2005) 21st Edition, Philadelphia, Pa. Lippincott Williams & Wilkins. In certain aspects the formulations comprise a ratio of DI particles to infectious particles. In certain embodiments the ratio of DI particles to infectious particles is decreased, relative to the ratio of DI particles to infectious particles that are produced by unmodified arenavirus. However, regardless of the composition of DI particles to infectious virus in the preparation, these modified viruses, once they infect a new host, are expected to produce a greater quantity of DI particles vs infectious particles, which is believed to be important for the attenuation of their ability to efficiently spread in the host. Thus, in certain aspects the disclosure provides a pharmaceutical formulation comprising live (not inactivated) virus. In embodiments, the virus is attenuated in that once it is placed in an environment lacking artificial kinase inhibition, i.e., a population of viral particles is introduced into a human or non-human animal individual, the viral particles that are produced are predominantly DI particles, and/or more DI particles are produced when the arenaviruses are placed in the environment lacking artificial kinase inhibition, relative to DI particle production in the environment with the artificial kinase inhibition.

Administration of pharmaceutical formulations comprising the modified arenaviruses as described herein can be performed using any suitable route of administration, including but not limited to parenteral, intraperitoneal, intrapulmonary, oral, and intra-tumoral. Parenteral infusions include intramuscular, intravenous, intraarterial, intraperitoneal, and subcutaneous administration. The compositions can be administered to humans, and are also suitable for use in a veterinary context and accordingly can be given to non-human animals, including non-human mammals.

In embodiments the modified arenaviruses are used to treat cells that have been separated from an individual. For example, cells are separated from an individual and are contacted with the modified arenaviruses such that the modified arenaviruses enters into the cells, after which the cells are reintroduced to the individual. In embodiments, cells treated according to this approach comprise antigen presenting cells, including but not necessarily limited to dendritic cells and macrophages.

The following Examples are intended to illustrate but not limit embodiments of this disclosure.

Example 1

This Example demonstrates that the LCMV matrix protein is reversibly phosphorylated.

The matrix protein plays a multifactorial role in the arenavirus life cycle yet little is known regarding how its various functions are regulated. In an effort to analyze this, LCMV strain Armstrong 53b particles grown in Vero E6 cells were purified via sucrose-banding (FIG. 1A) and subjected to mass spectrometry. This analysis revealed a tyrosine phosphorylation site near the C-terminus of the LCMV Z protein at position 88 (Y88) (FIG. 1B and S1), which lies within LCMV Z's late domain (FIG. 1C). Both phosphorylated and unphosphorylated peptides containing this residue were observed at a ratio of 1 to 11, respectively, which suggests that ~10% of the total Z protein in this virion preparation is phosphorylated (FIG. 1B and S1C). Because the virion preparation contained a mixture of both standard infectious virus and DI particles, we were not able to determine whether the phosphorylated Z was derived from standard particles, DI particles, and/or both types of particles. To confirm the phosphorylation site, plasmids encoding either WT Z or a phenylalanine mutant (Y88F) that cannot be phosphorylated were transfected into HEK293T cells and 2 days later the cells were treated with either water or the tyrosine phosphatase inhibitor, hydrogen peroxide. WT Z and Y88F Z were affinity purified and probed with a phosphotyrosine-specific antibody. The phosphotyrosine signal detected from WT Z was greatly enhanced following inhibition of tyrosine phosphatases (FIG. 1D). Substitution of tyrosine 88 with phenylalanine, to prevent phosphorylation, resulted in a complete loss of detectable phosphotyrosine signal in both settings indicating that Y88 may be the only tyrosine of the 3 encoded in LCMV Z that is phosphorylated (FIG. 1D) by endogenous kinases in these cells. To determine whether LCMV Z is tyrosine phosphorylated in the context of a relevant rodent cell line, we infected murine L929 cells with a rLCMV that encodes Z with a C-terminal streptavidin binding peptide (SBP) tag. Two days later, cells were either treated with hydrogen peroxide or not and Z was affinity purified from cell lysates for western blot analysis. As shown in FIG. 1E, a phosphotyrosine signal was clearly detectable from Z and was enhanced following treatment with hydrogen peroxide.

Example 2

This Example demonstrates the LCMV matrix protein PPXY late domain is dispensable for the production of standard infectious particles.

The finding that LCMV Z is phosphorylated at Y88 was intriguing as this residue is part of LCMV's only late domain, PPPY. This motif is well conserved among most Old World arenavirus Z proteins (FIG. 2A) and its importance for the budding activity of LCMV and Lassa virus Z in the context of VLP-budding assays has been described. To investigate the role of this late domain in the context of authentic virus and to determine whether tyrosine phosphorylation may regulate its function, we generated recombinant (r)LCMV encoding either phenylalanine or alanine at position 88 to prevent phosphorylation at this site or glutamic acid to mimic constitutive phosphorylation. The alanine mutant was included as a reference to previous studies on the function of this late domain for LCMV and Lassa virus Z, which used alanine substitutions at Y88 to assess the contribution of this late domain to Z's budding efficiency in VLP assays. Viruses containing all three mutations were recoverable despite the well-described defect in Z's budding efficiency caused by mutation of this residue (FIG. 2B). The growth kinetics of rLCMV Z-Y88F and Z-Y88A during the first 36 hours (hr) post-infection (pi) were nearly identical, but impaired ~15-fold compared to rLCMV WT (P≤0.0001; FIGS. 2B and 2C). The growth rate of the rLCMV Z-Y88E phosphomimetic was also attenuated compared to WT virus over this same time frame (~4-fold less PFU at 36 hr pi, P≤0.05, FIGS. 2B and 2C). However, the phosphomimetic virus grew to ~4-fold higher titers than the alanine or phenylalanine mutants (P≤0.01; FIGS. 2B and 2C). Additionally, the mean plaque size for rLCMV Z-Y88E was significantly increased compared to the Z-Y88F and Z-Y88A viruses (0.67 vs 0.53 or 0.52 mm$^2$; P≤0.01; FIG. 2D), indicating that virus spread was partially restored in the phosphomimetic virus. Notably, each mutant virus eventually reached peak WT titers. Given the delayed kinetics observed in the mutant viruses, we tested for reversion mutations at 72 hr pi and confirmed that each virus retained its respective mutated residue at position 88 and its small plaque phenotype (FIG. 2D). Collectively, these results demonstrate that the PPXY late domain is not absolutely required for the formation and release of standard infectious particles. Further, phosphorylation of Y88 may have a positive regulatory impact on viral propagation.

Example 3

This Example demonstrates that phosphorylation of the PPXY late domain does not enhance Z's ability to form VLPs.

Point mutations made at Y88 suggested that dynamic phosphorylation of this residue was important for the function of the matrix protein. We next investigated the specific effect these point mutations had on Z's budding efficiency in a VLP release assay. Because the LCMV Z protein is sufficient for the production of VLPs in the absence of any other viral proteins, we were able to assess the budding activity of plasmid-derived WT or Y88-mutant Z proteins. As a control, we also included the LCMV Z G2A mutant, which exhibits a pronounced defect in VLP formation due to its inability to be myristoylated at this glycine residue. HEK293T cells were transfected with plasmids encoding WT or Y88 mutants and 1 day later the VLP-containing supernatant and cells were collected and analyzed by quantitative western blotting. The budding activity of all three Z Y88 mutants was significantly reduced compared to WT Z, indicating that mutations in this region reduce the efficiency of VLP release (FIG. 2E). We did not observe a significant difference between the budding of the Z-Y88E phosphomimetic compared to Y88F and Y88A (FIG. 2E). This suggests that the partial gain of fitness observed with the phosphomimetic rLCMV-Z-Y88E virus in FIG. 2B is not due to an increase in budding activity and as such Y88 phosphorylation does not appear to directly regulate the budding function of this late domain.

Example 4

This Example demonstrates that PPXY late domain mutant viruses release substantially less viral structural proteins and genomes without a corresponding loss of infectious units.

To investigate the protein and genome composition of virions containing mutated late domains, an equivalent quantity of cell-free infectious virus particles from each rLCMV strain was concentrated for screening. Quantitative western blotting revealed substantial reductions in the total amount of NP, GP, and Z in the Y88 mutant particles relative to WT virus (FIGS. 3A-3D). However, no difference was observed in the levels of these proteins among the three Y88 mutant viruses (FIGS. 3A-3D). The quantity of Z protein detected in the Y88 mutant virus preparations was <3% of WT virus (FIG. 3D) whereas NP and GP quantities were ~25% of WT virus (FIGS. 3B and 3C). Viral genome content in particles was assessed by qRT-PCR. On a per PFU basis, the quantity of either L or S segment genomic RNA in the non-phosphorylatable mutants, Y88F and Y88A, was significantly reduced versus WT (P≤0.05, FIGS. 3E and 3F). However, genome levels in the phosphomimetic virus, Y88E, were not significantly different than WT (FIGS. 3E and 3F), which may explain a component of its partially restored growth kinetics (FIG. 2B). The observation of reduced viral proteins and/or genomes released from cells infected with the Y88 mutant viruses combined with the fact that WT LCMV is known to produce relatively large quantities of DI particles led us to hypothesize that the PPXY mutants may have defects in their ability to generate DI particles, which could explain their greatly reduced levels of viral protein and genome relative to PFU.

Example 5

This Example demonstrates that the PPXY late domain drives the production of DI particles.

A substantial fraction of virus particles produced by LCMV are DI particles. Accordingly, inoculation of LCMV at low multiplicities of infection (MOI) results in efficient production of standard virus and spread, while high MOIs do not. This seemingly contradictory phenomenon is caused by DI particles, which inhibit the propagation of standard virus and its ability to cause cytopathic effect with one hit kinetics. Monolayers inoculated with high concentrations of standard infectious LCMV exhibit no cytopathic effect due to DI particle inhibition, but as the inoculum is diluted, standard virus particles that infect cells in the absence of a co-infecting DI particle will subsequently form plaques. We exploited this phenomenon to initially evaluate the relative amounts of DI particles generated by the PPXY mutant viruses. Equal infectious doses of WT virus and each Y88 mutant, spanning a range of 25 to 25,000 PFU, were applied to Vero E6 cell monolayers in a standard plaque assay (FIGS. 4A and 4B). Evidence of possible DI particle interference is clearly seen in WT virus, where the most concentrated viral sample (25,000 PFU) resulted in no cell death while in successive 10-fold dilutions (2,500 and 250 PFU) the number of DI particles per cell is lowered allowing standard virus to enter cells in the absence of DI particles and form plaques (FIG. 4A). In contrast, the PPXY-mutant viruses exhibited a considerable increase in cytopathology (FIG. 4A, 25,000 and 2,500 PFU). Quantification of the observed cytopathology confirmed the striking phenotype and revealed significant differences between the mutant and WT viruses (FIG. 4B). Intriguingly, the cytopathology of the rLCMV Z-Y88E phosphomimetic at 25,000 PFU was significantly less than both Y88F or Y88A viruses and therefore more closely resembled WT virus (FIG. 4B).

Figure 4:
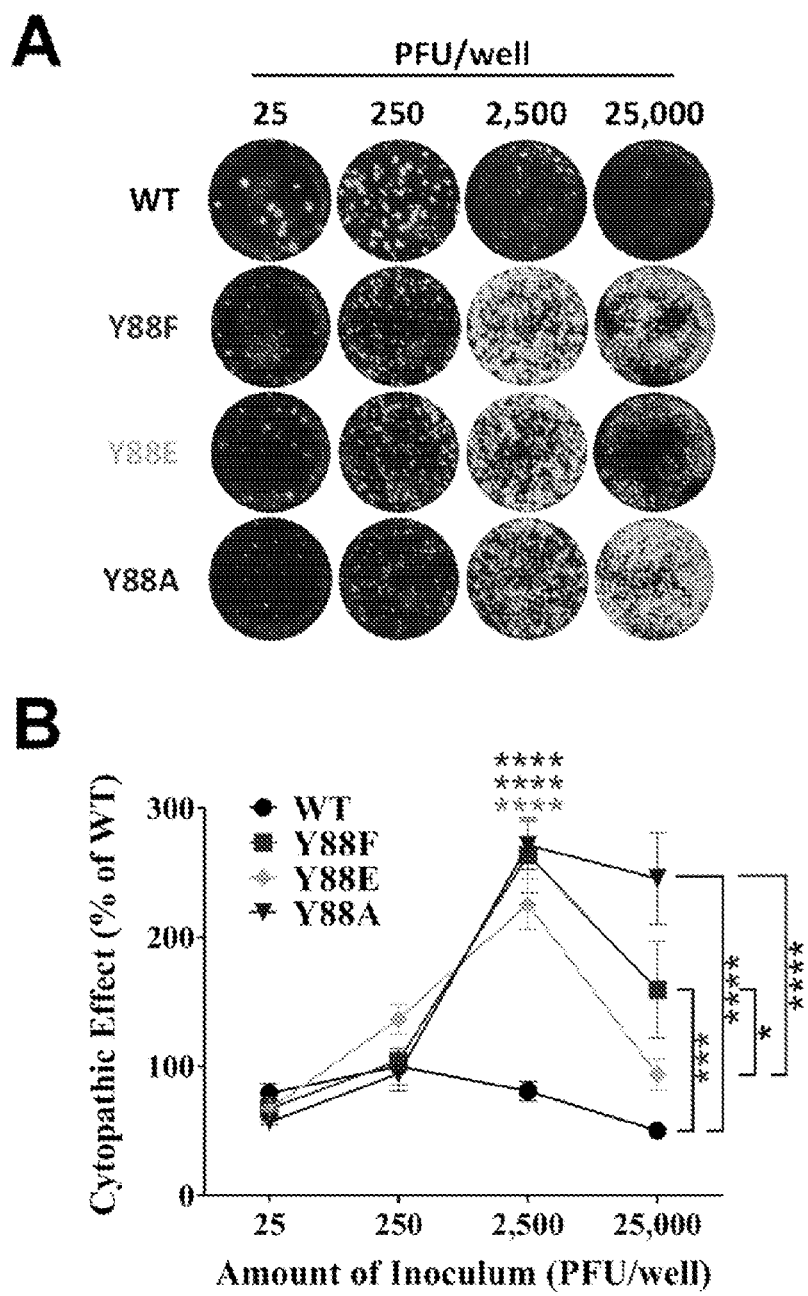
FIG. 4. LCMV DI particle production is impaired in the absence of a functional PPXY domain. (A-B) Equivalent PFUs of WT, Z Y88F, Z Y88E, or Z Y88A rLCMV (range 25 to 2.5×10$^4$ PFUs) were inoculated onto monolayers of Vero E6 cells and a standard plaque assay was performed. Representative images of crystal violet-stained wells are shown in (A). Inhibition of standard infectious virus-induced cytopathic effect by DI particles at each dose was determined by measurement of the mean pixel intensity of each well using Image J software (B). The data in (B) are representative of the mean±SEM relative to rLCMV WT (at 250 PFU per well) from 3 independent experiments and were tested for statistical significance with a two way ANOVA and Holm-Sidak's test for multiple comparisons. B) *$p<0.05$; *$p<0.001$; **$p<0.0001$, as determined by the indicated statistical tests.
Figure 9:
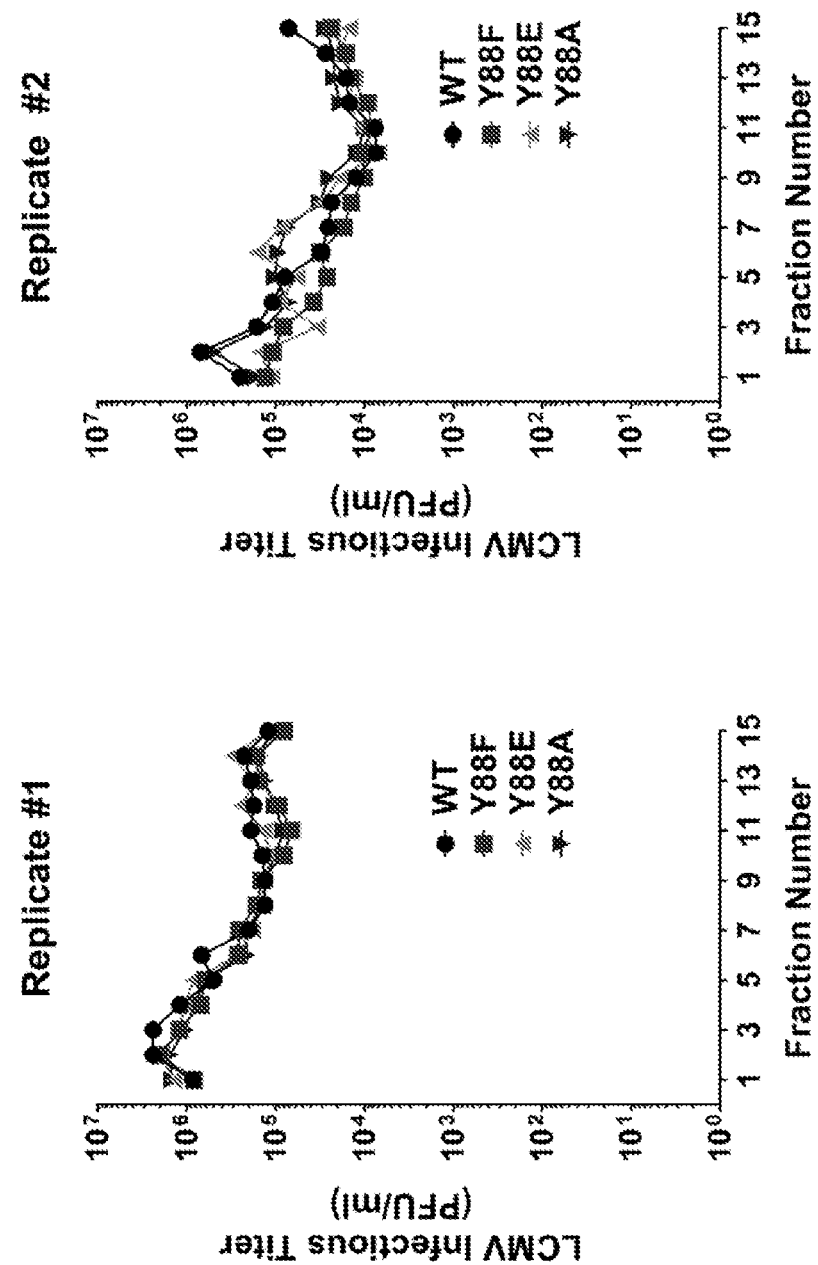
FIG. 9. Profile of standard infectious rLCMV WT or Y88 particles following separation via density ultracentrifugation. Vero E6 cells were infected with rLCMV WT, Y88F, Y88E, or Y88A at an MOI of 0.0001 and 72 hr later supernatants were clarified, precipitated with PEG-8000, resuspended in TNE, and titered for PFU via plaque assay. An equal number of PFU for each rLCMV was layered onto an optiprep gradient (7%, 10%, 13%, 16%, and 19%) and centrifuged for 12 hr at 30,000 RPM at 4° C. The entire gradient was collected in 15 fractions of 2 mL each. Each fraction was titered for PFU via plaque assay. Shown are results from 2 independent experiments.

To confirm that the interfering activity observed in FIG. 4 was indeed due to LCMV DI particles, we next established an assay to directly and quantitatively measure LCMV DI particle activity. At present, no consistent biochemical or genetic signature exists to distinguish LCMV DI particles from standard infectious particles. In an attempt to uncover such a signature, we separated preparations of rLCMV WT or Y88 mutants via density ultracentrifugation. We were unable to isolate fractions containing pure DI particles as abundant levels of standard virus were detectable across all 15 fractions (FIG. 9). Therefore, it was not possible to identify a DI particle-specific signature for screening purposes. Despite this limitation, several assays, including a yield reduction assay, a plaque reduction assay, and a focus interfering assay have historically been used for accurate measurement of LCMV DI particle abundance and activity levels. Indeed, these assays were originally used to define LCMV DI particles. We utilized the plaque interference assay (also known as the plaque reduction assay) analogous to that used in but also capitalized on the strong UV-resistance exhibited by LCMV DI particles, but not standard virus particles. Briefly, cell-free virus preparations containing both standard and DI particles were treated with UV to neutralize standard virus particles while leaving the interfering properties of DI particles intact (FIG. 5A). It should be noted that standard virus particles treated with UV do not acquire detectable interfering properties (FIG. 5A). Limiting dilutions of this UV-treated sample were applied to Vero E6 cells, followed by the addition of a fixed quantity of LCMV PFUs. As shown in FIG. 5A, this allows for the determination of LCMV DI particle activity and is expressed as plaque interfering units$_{50}$ (PIU$_{50}$) per mL of a given sample. Importantly, we recapitulated several key controls from previous studies to demonstrate the specificity of this assay for LCMV DI particles. In particular, UV-treated LCMV DI particle preparations only interfered, in a dose-dependent manner, with the growth of homologous LCMV, but not heterologous viruses such as vesicular stomatitis virus (VSV) or the New World arenavirus Junin virus Candid 1 (JUNV C#1), which rules out a nonspecific antiviral factor as a mediator of interference (e.g. interferon) (FIG. 5A). Further, passing LCMV DI particle-containing supernatant through a series of filters (0.45 µm, 0.2 µm, 30 kDa, 10 kDa) showed that interference is not due to soluble factors that are smaller than 30 kDa (e.g. cytokines) or larger (>0.2 µm) membrane bound entities such as bacteria (FIG. 5B). When this assay was applied to the rLCMV WT and Y88 mutant samples examined in FIG. 4, it confirmed that the rLCMV WT samples exhibited substantial DI particle interfering activity (mean 926 PIU$_{50}$/mL±68 SEM), but that the mutant Y88 viruses had much less (FIG. 5C). There was no detectable DI activity for either the Y88F or Y88A viruses while the Y88E virus contained intermediate levels of interfering activity (mean 131 PIU$_{50}$/mL±64 SEM). Collectively, the findings in FIGS. 4 and 5 support the hypothesis that the LCMV PPXY late domain is required for the efficient formation of DI particles and that phosphorylation of Y88 may play a regulatory role in DI particle production and the inhibition of cytopathic effect.

Example 6

This Example shows that efficient DI particle formation requires a functional ESCRT pathway.

Figure 6:
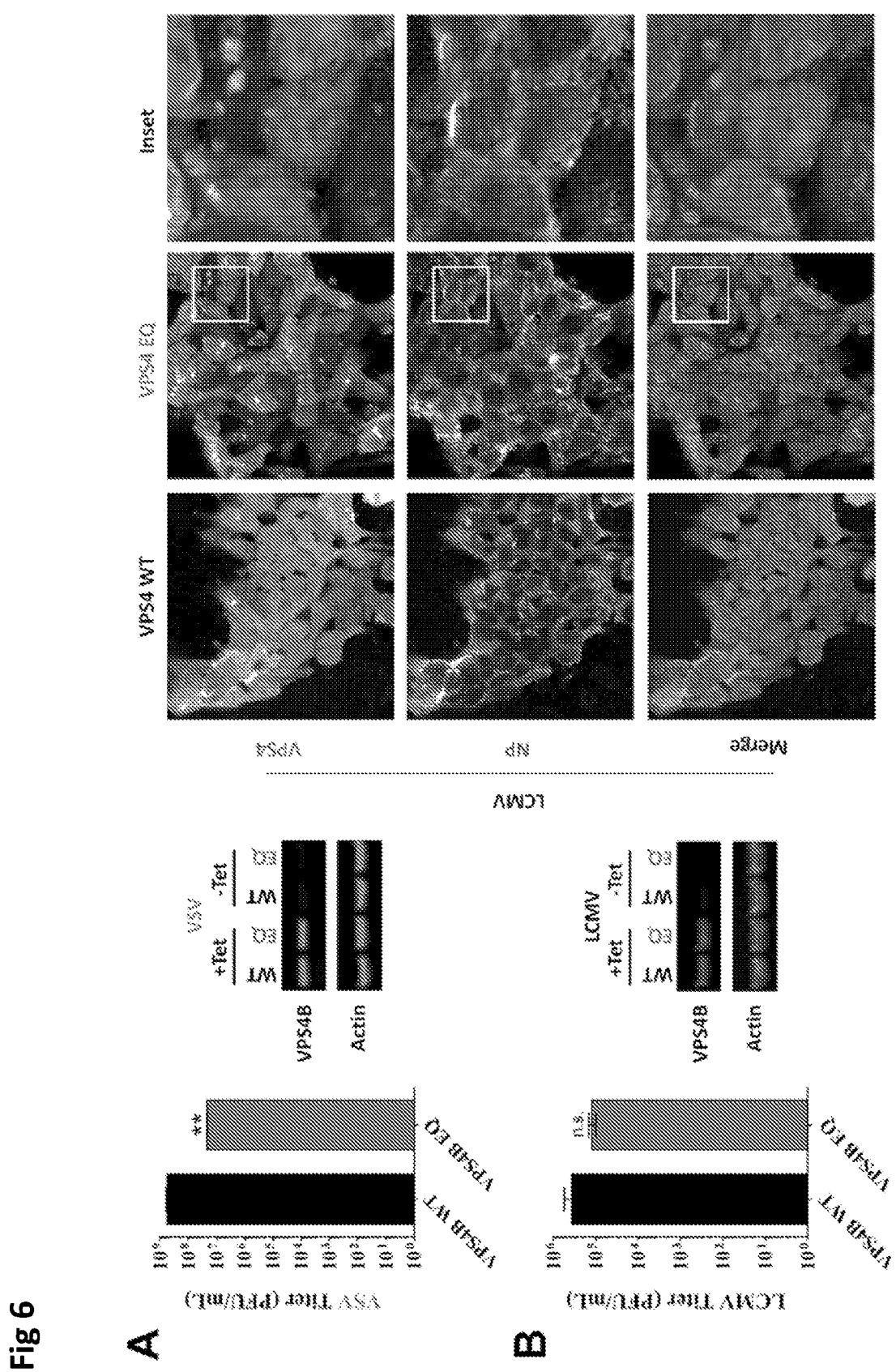
FIG. 6. Efficient DI particle formation requires a functional ESCRT pathway. (A) VSV requires a functional ESCRT pathway for infectious virus release. T-Rex HEK293 cells stably transduced with vectors for tetracycline-based induction of WT vacuolar protein sorting 4B (VPS4B) or the DN VPS4B mutant, EQ, were treated with tetracycline to induce the expression of WT or DN VPS4B. Both the WT and DN VPS4B proteins have GFP fusion tags. One hr following VPS4B induction, the media was removed and cells were infected with VSV in media containing tetracycline. One hr later, the viral inoculum was removed and replaced with fresh media containing tetracycline. Six hr later (8 hr post-VPS4B induction; 7 hr post-infection), supernatants were collected to determine VSV PFU titers via plaque assay. Cell protein lysates were also generated at this time to verify the induction of VPS4B WT or EQ expression using an anti-GFP antibody. Protein lysates were also screened for actin as a loading control. Viral titers represent the mean VSV PFU±SEM from 3 independent experiments and were tested for statistical significance with an unpaired t test with Welch's correction. (B-E) LCMV requires a functional ESCRT pathway for the release of DI particles, but not standard infectious particles. T-Rex HEK293 cells stably transduced with vectors for tetracycline-based induction of WT VPS4B or the DN VPS4B EQ were infected with rLCMV WT and 2 d later treated with tetracycline to induce the expression of WT or DN VPS4B. Six hr after VPS4B induction (54 hr pi), the cells were washed and given fresh media containing tetracycline. Supernatants were collected 18 hr later (72 hr pi) and titered via plaque assay. Similar to (A), protein lysates were collected at 72 hr pi and screened for VPS4B WT or DN using an anti-GFP antibody or for actin as a loading control. Extra wells containing cells grown on cover slips were also fixed at 72 hr pi to examine, via immunofluorescent confocal microscopy, the expression and localization of WT or DN VPS4B (green) or LCMV NP (red). A 143 µm square is shown for each panel. The results shown in (B) represent the mean LCMV PFU±SEM from 4 independent experiments and were tested for statistical significance with an unpaired t test with Welch's correction. (C) Equivalent PFUs of virus (range $2 \times 10^2$ to $2 \times 10^4$) produced from WT or DN VPS4B cells were inoculated onto monolayers of Vero E6 cells and a standard plaque assay was performed. Representative images of crystal violet-stained wells are shown in (C). Inhibition of standard infectious virus-induced cytopathic effect by DI particles at each dose was determined in (D) by measurement of the mean pixel intensity of each well using Image J software. The data in (D) are representative of the mean±SEM relative to WT VSP4B (at 2,000 PFU per well) from 4 independent experiments and were tested for statistical significance with a two way ANOVA and Holm-Sidak's test for multiple comparisons. (E) The assay described in FIG. 5 was used to directly measure the LCMV DI titer present in the supernatants collected from the VSP4B WT or DN cells at 72 hr pi. Briefly, each virus-containing preparation was subjected to UV-irradiation to inactivate standard infectious LCMV particles while preserving DI particle activity. Serial 5-fold dilutions of each UV-treated sample were inoculated onto Vero E6 cells, followed by the addition of 50 PFU of standard LCMV. Following a 1 hr incubation at 37° C. to permit viral particle absorption, cells were overlaid with agarose and subsequently fixed and stained with crystal violet to visualize whether the various UV-treated rLCMV preparations impacted the ability of standard LCMV particles to form plaques. The LCMV DI titers are reported as mean PIU50/mL±SEM for 4 independent experiments and were tested for statistical significance with an unpaired t test with Welch's correction. (A-B, D-E) n.s. (not significant), *p<0.05, **p<0.01, as determined by the indicated statistical tests.
Figure 10:
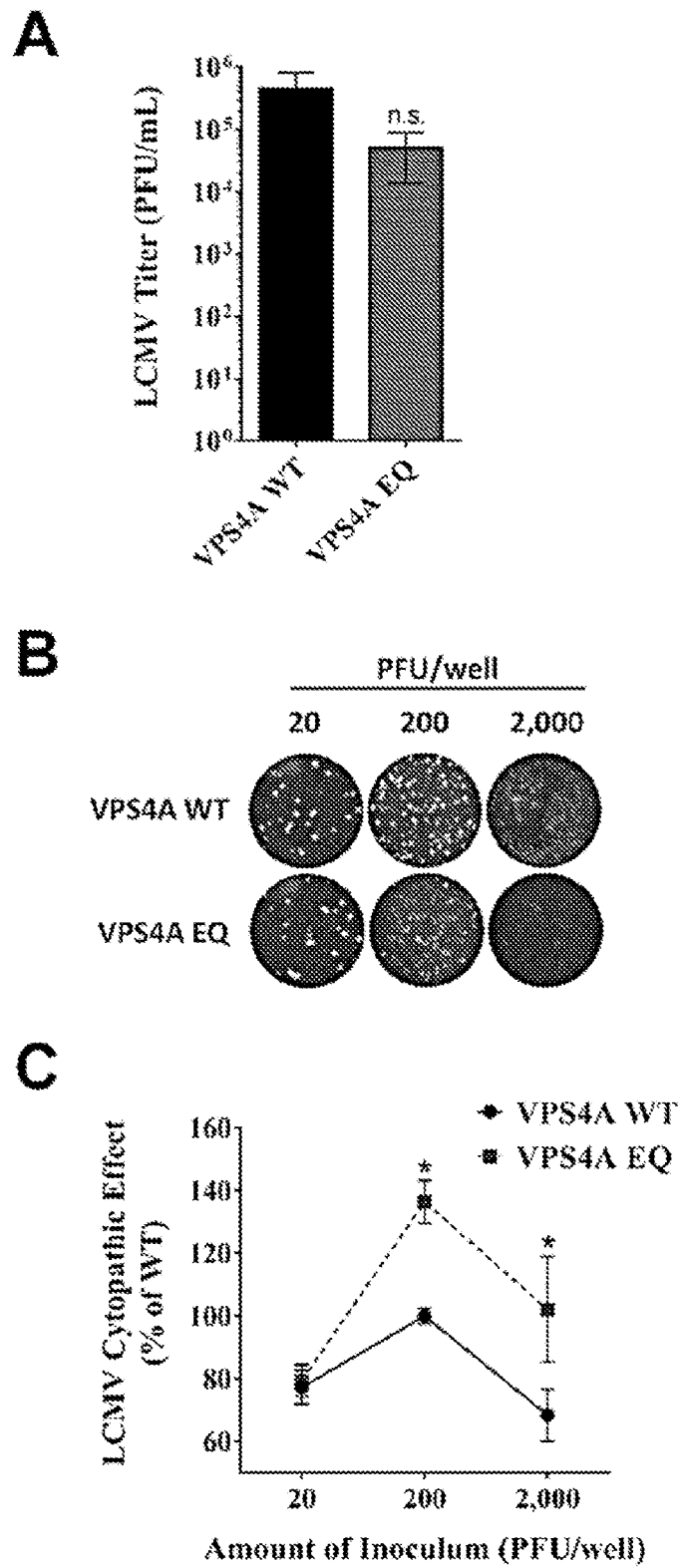
FIG. 10. Efficient DI particle formation requires a functional ESCRT pathway. (A-C) T-Rex HEK293 cells stably transduced with vectors for tetracycline-based induction of WT vacuolar protein sorting 4A (VPS4A) or the DN VPS4A mutant, EQ, were infected with rLCMV WT and 2 d later treated with tetracycline to induce the expression of WT or DN VPS4A. 6 hr after VPS4A induction (54 hr pi), the cells were washed and given fresh media containing tetracycline. Supernatants were collected 18 hr later (72 hr pi) and titered via plaque assay. The results shown in (A) represent the mean PFU±SEM from 2 independent experiments that contained 3 technical replicates and were tested for statistical significance with an unpaired t test with Welch's correction. Equivalent PFUs of virus (range 2×101 to 2×103) produced from WT or DN VPS4A cells were inoculated onto monolayers of Vero E6 cells and a standard plaque assay was performed. Representative images of crystal violet-stained wells are shown in (B). Inhibition of standard infectious virus-induced cytopathic effect by DI particles at each dose was determined in (C) by measurement of the mean pixel intensity of each well using Image J software. The data in (C) are representative of the mean±SEM relative to WT VSP4A (at 200 PFU per well) from 2 independent experiments that contained 3 technical replicates and were tested for statistical significance with a two way ANOVA and Holm-Sidak's test for multiple comparisons. (C) *$p<0.05$, as determined by the indicated statistical tests.
Figure 11:
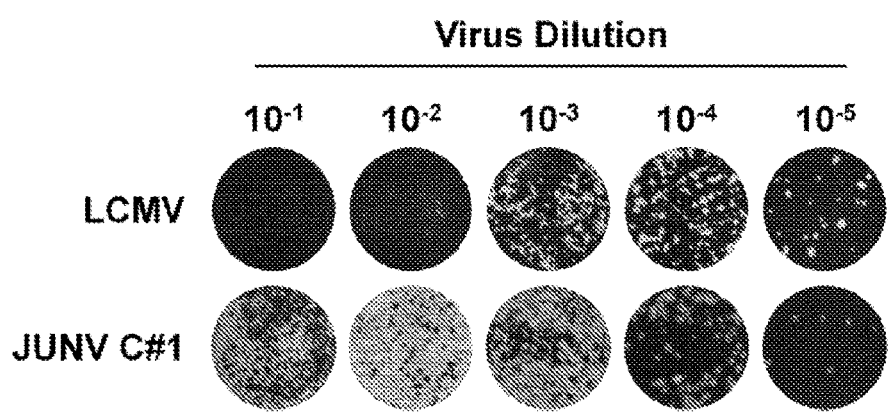
FIG. 11. LCMV generates more DI particles per standard infectious particle than JUNV C#1. Serial 10-fold dilutions of stock preparations of LCMV or JUNV C#1 were inoculated onto monolayers of Vero E6 cells and a standard plaque assay was performed to visualize DI-mediated interference of standard virus at low dilutions.
Figure 12:
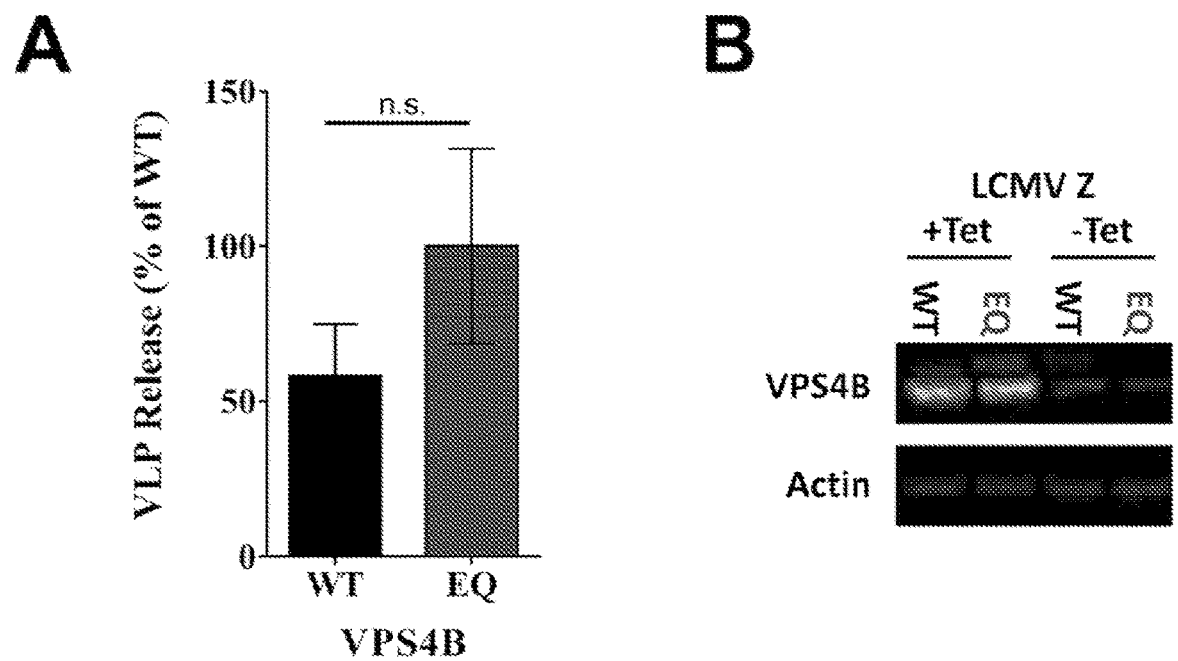
FIG. 12. Expression of dominant negative VPS4B does not impact the ability of LCMV Z to form VLPs. (A-B) T-Rex HEK293 cells stably transduced with a tetracycline-inducible plasmid encoding WT or dominant negative EQ mutant vacuolar protein sorting 4B (VPS4B) were simultaneously transfected with a plasmid encoding LCMV Z WT and exposed to tetracycline to drive the expression of WT or DN VPS4B. One day later both the cells and VLP-containing supernatants were collected. Z from VLP-containing supernatants was affinity purified with magnetic streptavidin beads. The quantity of Z affinity purified from VLPs or present in the corresponding whole cell lysates was determined via quantitative western blotting. The percent VLP release shown in (A) was calculated as the amount of Z protein found in the cell culture media relative to the amount in cells. Data are presented as mean release±SEM relative to WT Z from 3 independent experiments. A one way ANOVA with Holm-Sidak's test for multiple comparisons was used to compare the mean values. n.s., not significant). In panel (B), cell lysates were also screened by western blotting to verify the induction of VPS4B WT or EQ expression using an anti-GFP antibody and for actin as a loading control.

Viral late domains can drive virus budding by recruiting components of the cellular ESCRT pathway to complete the final membrane scission step. Given the role that the LCMV PPXY late domain played in the production of DI particles (FIGS. 4A, 4B, and 5C), we hypothesized that this late domain might be recruiting the ESCRT pathway machinery to drive DI particle formation. To test this hypothesis, we utilized cell lines that lack a functional ESCRT pathway due to inducible expression of a dominant negative (DN), E235Q point mutant, of VPS4, an ATPase involved in the final stages of ESCRT pathway function. Because the ESCRT pathway can also affect LCMV entry, we first infected cells with LCMV for 48 hr to allow the entire monolayer to become infected before inducing expression of WT or DN VPS4. The cells were washed and fresh media containing the induction agent was added to the cells 6 hr after initial induction (54 hr pi) and the virus-containing media was collected 18 hr later (72 hr pi) to determine levels of standard infectious particles and DI particles (FIG. 6). Western blot analysis of protein lysates at 72 hr pi confirmed the strong induction of WT and DN VPS4B expression and examination of fixed coverslips showed that all cells were expressing both the induced VSP4B as well as LCMV NP (FIG. 6B). This infection protocol was chosen to ensure that we were examining virus that was produced in cells expressing the induced VPS4B proteins, while minimizing the effect that these proteins could exert on viral entry. Expression of DN VPS4B had no impact on the release of standard infectious LCMV (P=0.27; FIG. 6B). In contrast, expression of DN VPS4B led to a marked reduction in the release of infectious VSV particles (FIG. 6A), which confirms the specificity of our findings for LCMV. Measuring LCMV DI particle activity as described in FIG. 4 revealed that WT LCMV produced considerably fewer DI particles per standard infectious virus particle in the DN VPS4B background when compared to cells expressing WT VPS4B (FIGS. 6C and 6D). A similar trend for both LCMV infectious virus and DI particle activity was seen in cells expressing WT or DN VPS4A (FIG. 10). We next used the assay described in FIG. 5 to directly quantitate the LCMV DI particle activity in these samples. Consistent with the findings in FIGS. 6C and 6D, this demonstrated that significantly fewer DI particles are made in the context of the DN VPS4B background when compared to WT VPS4B (mean 41±6 SEM vs 1,491±70 $PIU_{50}$/mL, respectively; P=0.0022). Thus it appears that LCMV DI particle formation requires a functional ESCRT pathway (FIGS. 6C-6E) in addition to a canonical late domain (FIGS. 4 and 5C) while standard particles do not (FIG. 6B).

Figure 7:
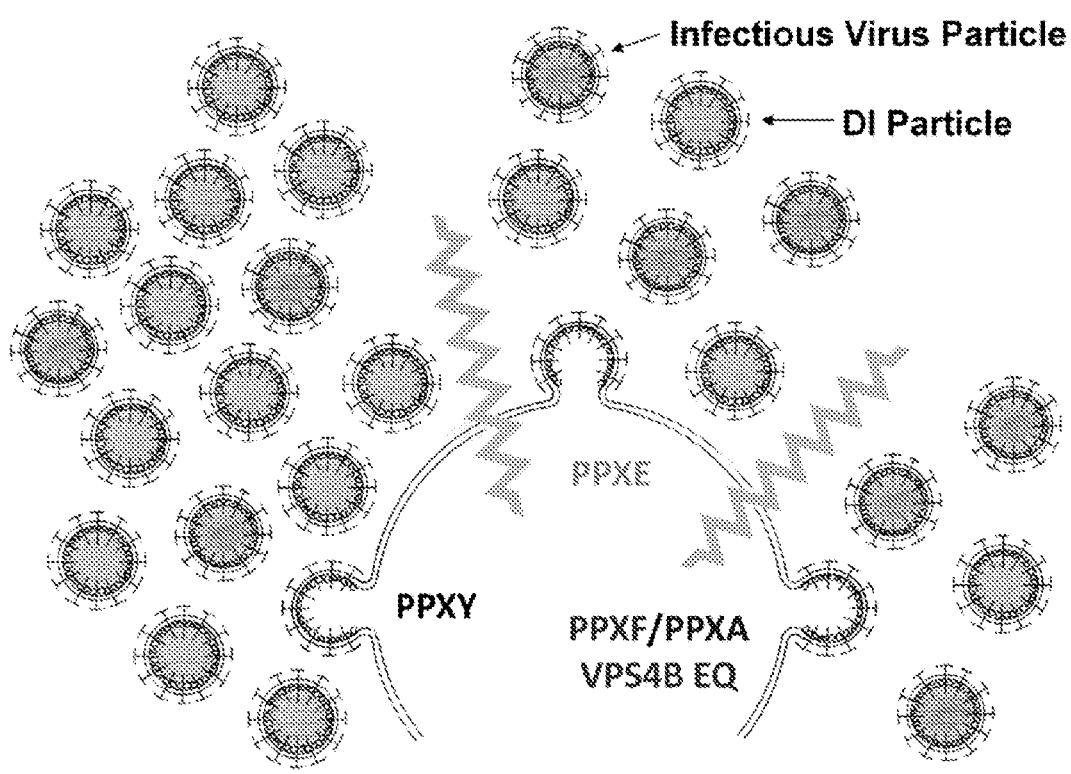
FIG. 7. Proposed and non-limiting model of PPXY-driven DI particle production. WT virus containing an intact PPXY late domain produces high levels of infectious and DI particles. Disruption of the PPXY motif (PPXF or PPXA) or disruption of the ESCRT pathway causes decreased overall DI particle production compared to standard infectious particles. The phosphomimetic PPXE virus has an intermediate phenotype.

In view of the foregoing it will be apparent that the present specification demonstrates that the PPXY late domain encoded by LCMV is not absolutely required for infectious virus release, and that infectious particle release can occur in the absence of a functional ESCRT pathway. It is shown that the formation of LCMV DI particles requires a functional PPXY late domain and that this process is ESCRT-dependent (see FIG. 7 for our proposed model, which is meant for illustration and is not intended to be limiting). Our data demonstrate that the terminal tyrosine in the LCMV PPX<u>Y</u> motif is phosphorylated and that this posttranslational modification likely experts a regulatory effect on Z's ability to drive DI particle release. Therefore, we have uncovered an unexpected role for the PPXY late domain and a possible mechanism for its regulation of DI particle production. In particular, and in contrast to standard virus particles, both the PPXY late domain and the ESCRT pathway appear critical for the release of DI particles. To our knowledge, this is the first example of a virus utilizing a late domain to selectively drive the production of DI particles independently of standard virus. The data demonstrate that cells infected with the rLCMV PPXY mutants release much less NP, GP, and Z per PFU of cell-free virus when compared to WT rLCMV. This is presumably due to reduced levels of DI particles being released by the PPXY mutant viruses. Interestingly, the degree of reduction was not equivalent among the viral proteins. In particular, Z was reduced to the greatest extent (~3% of WT) when compared to NP or GP (~25% of WT), which could indicate that Z itself is enriched in DI particles and is critical for the ability of DI particles to interfere with the propagation of standard virus particles. We show that the LCMV Z protein is phosphorylated, which suggests that phosphorylation may be important for the regulation of one or more of Z's functions. The fact that this modification occurs at the terminal tyrosine of the PPXY late domain and can be detected in virion-derived Z led us to hypothesize that it may influence Z's budding function. To study the impact of this modification we generated rLCMV with mutations at tyrosine 88 that either prevented phosphorylation (Y88F or Y88A) or mimicked it (Y88E). Relative to the mutants that cannot be phosphorylated, the Y88E phosphomimetic virus generated significantly more DI particles per infectious particle (FIGS. 4 and 5C). This indicates that reversible phosphorylation of the PPXY motif may act as a rheostat to regulate the rate of DI particle production independent of standard virus, possibly through the recruitment of ESCRT machinery.

Example 7

This Example provides a description of the materials and methods used to obtain the data presented in Examples 1-6.

Cells and viruses. Human embryonic kidney cells (HEK-293T/17) (CRL-11268, American Type culture Collection, Manassas, Va.) (referred to as HEK293T cells in the manuscript) were maintained in Dulbecco's Modified Eagle Medium (DMEM) (11965-092) supplemented with 10% fetal bovine serum (FBS) (16140-071), 1% penicillin-streptomycin (15140-122), 1% MEM Non-Essential Amino Acids Solution (11140-050), 1% HEPES Buffer Solution (15630-130), and 1% GlutaMAX (35050-061) purchased from Invitrogen (Carlsbad, Calif.). L929 mouse fibroblast cells (CCL-1, American Type culture Collection) were maintained in Minimum Essential Medium (MEM) (11095-080) supplemented with 10% FBS, 1% penicillin-streptomycin, 1% MEM Non-Essential Amino Acids Solution, 1% HEPES Buffer Solution, and 1% GlutaMAX. Baby hamster kidney cells (BHK-21) were grown in DMEM supplemented with 10% FBS, 1% penicillin-streptomycin, and 1% GlutaMAX. African green monkey kidney cells (Vero E6) grown in DMEM supplemented with 10% FBS, 1% penicillin-streptomycin, and 1% HEPES Buffer Solution. T-Rex HEK293 cells stably transduced with a tetracycline-inducible plasmid encoding WT or dominant negative EQ mutant vacuolar protein sorting 4A (VPS4A) or VPS4B were maintained in DMEM supplemented with 10% FBS, 1% penicillin-streptomycin, 1% MEM Non-Essential Amino Acids Solution, 1% HEPES Buffer Solution, 1% GlutaMAX, and 100 µg/mL Zeocin (R250-01, Invitrogen). VPS4 expression was induced by incubating cells in the above growth medium containing 1 µg/mL tetracycline using established techniques. All cell lines were grown at 37° C. in a humidified incubator containing 5% $CO_2$. Working stocks of viruses were amplified and titered (via plaque assay) on Vero E6 cells. See below under "Generation of Recombinant LCMV" for a description of the recombinant (r)LCMV strain Armstrong 53b that were generated for this study.

Plasmids. The LCMV Armstrong 53b Z protein (WT, Y88A, Y88E, or Y88F) was subcloned into a modified pCAGGS expression vector and different combinations of these plasmids were used to screen for the phosphorylation of Z (FIG. 1D) or the budding efficiency of Z (FIG. 2E). The WT and Y88 mutant Z genes were fused to the streptavidin binding peptide (SBP) (MDEKTTGWRGGHVVEG-LAGELEQLRARLEHHPQGQREP) (SEQ ID NO:28) through an 18 base pair linker at the C-terminus of Z to permit affinity purification and western blot detection of Z. The nucleotide sequence of the WT Z gene matches NCBI gene identifier number AY847351 while the translated amino acid sequence for the WT Z gene matches Protein Locus number AAX49343. WT Z was amplified by PCR from the pT7-L(+) using the forward primer LCMVZf (5'-ACAAGTTTGTACAAAAAAGCAGGCTGA-TATCGCCACCATGGGTCAAGGCAAGTCCA GA-3') (SEQ ID NO:29), which has a 5' overhang containing Gateway AttB1 and Kozak sequences and the reverse primer LCMVZr (5'-ACCTC-CACCTCCAGCTGCCTCTTCGTAGGGAGGTGGAGA-3') (SEQ ID NO:30), which has an overhang containing the linker sequence. The SBP tag was amplified from the pT7-FLAG-SBP-1 plasmid (P3871, Sigma-Aldrich, St. Louis, Mo.) via PCR using the forward primer SBPf (5'-GCAGCTGGAGGTGGAGGTATGGACGAAAAAAC-CACCGGT-3') (SEQ ID NO:31), which has a 5' overhang containing the linker sequence, and the reverse primer SBPr (5'-ACCACTTTGTACAAGAAAGCTGGGTCT-TACGGTTCACGCTGACCCTGCGG-3') (SEQ ID NO:32), which contains a 3' overhang with a stop codon preceding an AttB2 sequence. The two products were fused by PCR using the Z forward primer and the SBPr primer. The cassette was subcloned into the pCAGGS vector using the Gateway cloning system (Invitrogen) following the manufacturer's instructions using established techniques. The plasmids pC-NP and pC-GP, which express the LCMV Armstrong 53b nucleoprotein (NP) and glycoprotein (GP), respectively, and plasmids pol-I S and pol-I L, which express the LCMV L and S genome segments, respectively, were used to generate rLCMV. Each of the Y88 mutant Z genes used in these studies were synthesized and subcloned into the pCAGGS or pol-I L vectors, respectively, by Biobasic, Inc. (Markham, ON, Canada). A pol-I L vector containing an SBP-tag directly fused to the C-terminus of Z was also generated by Biobasic, Inc. All plasmid sequences were verified by DNA sequencing.

Identification of phosphorylated residues by mass spectrometry. To identify phosphorylation sites on LCMV Z via mass spectrometry, Vero E6 cells were infected with LCMV strain Armstrong 53b and 48 hr later cell-free virions were purified by sucrose-banding using standard approaches. Purified virions were then lysed in Triton buffer (0.5% NP40, 1% Triton X-100, 140 mM NaCl, and 25 mM Tris-HCl containing a protease inhibitor cocktail (04693159001, Roche Applied Science, Indianapolis, Ind.)) and mixed with Laemmli sample buffer (62.5 mM Tris-HCl, 10% glycerol, 2% sodium dodecyl sulfate and 0.01% bromophenol blue (B392, Fisher Scientific, Pittsburgh, Pa.)) containing 5% 2-mercaptoethanol. Virion protein lysates were separated on a 4-20% Tris-Glycine polyacrylamide gel (EC60255, Invitrogen). The gel was stained with Coomassie (40% methanol, 20% acetic acid, and 0.1% Brilliant Blue R (B7920, Sigma-Aldrich)), destained with a solution of 30% methanol and 10% acetic acid, and then imaged using a Canon Canoscan 8800F scanner. For mass spectrometry, the protein band corresponding to the Z protein was excised and cut into 1 mm cubes and processed with chemicals from Fisher Scientific as follows. The gel pieces were rinsed with HPLC grade water and then incubated with destain solution (50 mM ammonium bicarbonate and 50% acetonitrile) for 30 minutes at 37° C. The destain solution was removed and the gel pieces were dehydrated by incubating twice with 100% acetonitrile for 5 minutes. The gel pieces were reduced with 25 mM dithiothreitol in 50 mM ammonium bicarbonate for 30 minutes at 55° C. After cooling for 10 minutes at room temperature, the gel pieces were dehydrated by incubating with 100% acetonitrile for 5 minutes and then alkylated in the dark with 10 mM iodoacetamide in 50 mM ammonium bicarbonate for 45 minutes at room temperature. The gel pieces were washed two times in destain solution for 5 minutes, dehydrated with 100% acetonitrile, then rehydrated with water for 10 minutes. The gel pieces were further dehydrated with two 5 minute incubations in 100% acetonitrile before removing all liquid and drying the gel pieces at room temperature for 10 minutes. The gel pieces were rehydrated with a solution of 12.5 ng/µL sequencing grade chymotrypsin (V1061, Promega, Madison, Wis.) or 12.5 ng/µL sequencing grade modified trypsin (V5111, Promega) in 50 mM ammonium bicarbonate on ice for 30 minutes, before digesting overnight at 37° C. Peptides were extracted with a solution of 2.5% formic acid in 50% acetonitrile while spinning in a microcentrifuge at 13,000 rpm for 10 minutes. The supernatant was removed and saved while the gel pieces were subjected to further extraction and rinsing with 100% acetonitrile. The second extraction was combined with the initial extraction. All solvent was removed from the extracts using a vacuum centrifuge at 37° C. The peptides were resuspended in 2.5% formic acid, 2.5% acetonitrile prior to mass spectrometry analysis. Peptides were separated over 12 cm of Magic C18, 5 µM, 200 Å reversed phase material (PM5/66100/00, Michrom Biore-sources, Auburn, Calif.) in a microcapillary column using a MicroAS autosampler (Thermo Scientific, Pittsburgh, Pa.). Following 15 minutes of isocratic loading in 2.5% acetonitrile, 0.15% formic acid, the peptides were eluted from the column with a 5-35% gradient of acetonitrile with 0.15% formic acid over 40 minutes using a Surveyor Pump Plus HPLC (Thermo Scientific). Mass spectra were acquired either in an LTQ-XL linear ion trap, or in a linear ion trap-orbitrap mass spectrometer (Thermo Scientific). Briefly, for most analyses 10 data-dependent MS/MS spectra followed each survey scan. However, in several cases after obtaining the initial spectra for phosphopeptides we followed up with targeted MS/MS spectra in order to increase fragment ion coverage. The IPI human forward and reverse concatenated database was used to search the raw data using SEQUEST software requiring tryptic peptides and either a 2 Da precursor mass tolerance (for precursor data acquired in the LTQ) or 20 PPM (for precursor data acquired in the orbitrap). In the searches the following precursor mass differences were allowed: serine, threonine, and tyrosine residues (+79.96633 Da); methionine (+15.99492 Da) and cysteines (+57.02146 Da or 71.0371).

Validation of Z phosphorylation. To confirm that Z was phosphorylated in human cells as well as cells from rodent cells, in FIG. 1D-E, plasmid-derived Z expressed in HEK293T cells and Z from rLCMV Z-SBP-infected cells were both probed for phosphotyrosine signal via western blot. For plasmid-derived Z, $2 \times 10^5$ HEK293T cells were seeded in a 12-well plate and transfected the next day with 0.8 µg per well of pLCMV-Z WT, pLCMV-Z Y88F, or an empty vector using 0.8 µL of a 1 mg/mL solution of polyethylenimine (23966, Polysciences, Inc., Warrington, Pa.) per well. For Z derived from rLCMV Z-SBP-infected cells, $2.5 \times 10^5$ L929 cells were seeded in 6-well plates and infected the next day at an MOI of 0.01. Two days following the transfection or infection, $H_2O_2$ at a final concentration of 8.8 mM or an equivalent volume of $H_2O$ was spiked into the appropriate wells containing HEK293T or L929 growth media. After a 15 minute incubation, the cells were lysed in Triton buffer containing a protease inhibitor cocktail and PhosStop phosphatase inhibitor cocktail (04906837001, Roche Applied Science) and the SBP-tagged Z proteins were affinity purified using magnetic streptavidin beads using established techniques. The purified proteins were separated via SDS-PAGE and screened for Z or tyrosine phosphorylated-Z via standard chemiluminescent western blotting and detected with film (FIG. 1D) or with a LI-COR C-Digit digital imager (LI-COR, Lincoln, Nebr.) (FIG. 1E).

Generation of recombinant (r)LCMV. rLCMV WT, rLCMV Z-SBP and rLCMV containing Z-Y88 mutations (Y88F, Y88E, Y88A) were generated a known reverse genetics system. Briefly, 10 µL of Lipofectamine 2000 (52887, Invitrogen) was mixed with 100 µL of OptiMEM (31985, Invitrogen) and then added to a plasmid mixture consisting of 1.6 µg pC-NP, 2.0 µg pC-L, 1.6 µg pol-IS, and 2.8 µg pol-IL (WT, Z-SBP or containing the described Y88 point mutations) in 100 µL OptiMEM and incubated at room temperature for 25 minutes. 200 µL of this transfection mixture and 800 µL of OptiMEM was then added to 1 well of a 6-well plate which had been seeded the previous day with 3.5×105 BHK-21 cells and washed prior to transfection with 1 mL of OptiMEM. The cells were incubated with the transfection mixture for 4 hr after which the media was replaced with BHK-21 growth media diluted 5-fold in DMEM. Three days later the supernatant was collected, clarified by centrifugation at 1,200 RPM for 5 minutes at 4° C., and used to infect a fresh monolayer of 1.8×106 BHK-21 cells in a T-75 flask. Following a 1 hr absorption, the inoculum was removed and fresh BHK-21 growth media diluted 5-fold in DMEM was added to the cells. Three days later the supernatant of this flask was collected, clarified by centrifugation, and titered by plaque assay. To generate an expanded virus stock, Vero E6 cells were infected with this material at an MOI of 0.0001 and 48 or 72 hr later, supernatants were collected, clarified, and titered by plaque assay. A portion of the L segment (most of the Z gene, the intergenic region, and part of the L gene) of each rLCMV Y88 mutant was sequenced to ensure that these viruses had not reverted. The material used for this sequencing was derived from the 72 hr pi time point shown in FIG. 2B. Viral RNA from clarified supernatants was isolated using the Qiagen Viral RNA mini kit (52906, Qiagen, Valencia, Calif.) according to the manufacturer's protocol. Viral RNA was converted to cDNA using primer L 845– (5'-GCAGGACTT-GAGGGCTATGA-3') (SEQ ID NO:43), Superscript III (18080-044, Invitrogen), RNAse Out (10777-019, Invitrogen), and 5 μL of RNA following the manufacturer's protocol for first strand cDNA synthesis. A portion of the L-segment containing Z was amplified with 30-40 cycles of PCR using Platinum Pft DNA polymerase (11708-013, Invitrogen) and primers L126+ (5'-ATAGTA-CAAACAGGGCCGAAATCC-3') (SEQ ID NO:33) and L 764– (5'TTTGTTGGGTTCAGAGATAAGTGT-3') (SEQ ID NO:34) following the manufacturer's protocol. The PCR product was prepared for sequencing using ExoSAP-IT (78200, Affymetrix, Santa Clara, Calif.) following the manufacturer's protocol and sequenced by the University of Vermont Cancer Center DNA Analysis Facility.

SDS-PAGE and western blotting. Protein lysates were diluted in Laemmli sample buffer containing 5% 2-mercaptoethanol and separated on NuPAGE 4-12% Bis-Tris gels with MES buffer. Protein was transferred to nitrocellulose membranes using iBlot gel transfer stacks (M301001 or IB301002, Invitrogen) and the Invitrogen iBlot Device as directed by the manufacturer. Efficient protein transfer was confirmed by staining membranes with a solution containing 0.1% Ponceau S (P3504, Sigma-Aldrich) and 5% acetic acid which was subsequently removed by washing with water. Two methods were used for protein detection: quantitative LI-COR-based detection or standard chemiluminescent-based detection. For quantitative LI-COR analysis, membranes were blocked with a solution of 5% milk in PBS for 1 hr and incubated overnight at room temperature with the indicated primary antibodies diluted in PBS containing 5% milk and 0.2% Tween 20 (BP337, Fisher Scientific). Following 5 washes in PBS with 0.5% IGEPAL CA-630 (198596, MP Biomedicals, Solon, Ohio), the membranes were incubated for 1 hr at room temperature with secondary antibodies diluted in PBS containing 5% milk, 0.2% Tween 20 and 0.02% sodium dodecyl sulfate, washed 5 times in PBS with 0.5% IGEPAL CA-630 and 1 time with PBS, then imaged using the LI-COR Odyssey CLx imaging system. For quantitative LI-COR analysis of VPS4B in FIGS. 6A and 6B, membranes were probed using the iBind Flex western device (SLF2000, Thermo Scientific) with the iBind Flex fluorescent detection solution kit (SLF2019, Thermo Scientific) following the manufacturer's instructions. For chemiluminescent-based detection of phosphorylated proteins, the same general procedure was used with the following exceptions: i) membranes were blocked with either PBS containing 5% milk and 0.05% IGEPAL CA-630 or protein-free blocking buffer (37572, Thermo Scientific), ii) primary and secondary antibodies were diluted in PBS containing 5% milk, 0.05% IGEPAL CA-630, and 3% fetal bovine serum or protein-free blocking buffer, and iii) the secondary antibodies were incubated with the membrane for 2 hr.

The following primary antibodies were used for western blotting (at the indicated concentrations): mouse anti-streptavidin binding peptide (MAB10764, Millipore, Billerica, Mass.) (1:10,000), rabbit anti-actin (A2066, Sigma-Aldrich) (1:10,000), mouse anti-actin (A5441, Sigma-Aldrich) (1:5,000), rabbit anti-actin (A2066, Sigma-Aldrich) (1:2,500), mouse anti-phosphotyrosine (clone 4G10, Millipore) (0.2 μg/mL), mouse anti-green fluorescent protein (632380, Clontech, Mountain View, Calif.) (1:1,000), rabbit anti-LCMV Z (880) (1:500), mouse anti-LCMV GP2 (33.6) (1:2,000), and rabbit anti-LCMV nucleoprotein (2165) (1:5,000). Antibodies 880, 2165, and 33.6 were used. For quantitative western blotting, the following secondary antibodies from LI-COR were used: IRDye 800CW goat anti-mouse (926-32210) for the Z release assay in FIG. 2E at 1:20,000 and in FIGS. 6A and 6B at 1:3,000 (for probing by iBind) and IRDye 680LT goat anti-mouse (926-68020) and IRDye 800CW Goat anti-rabbit (926-32210) were used at 1:20,000 to detect proteins in FIGS. 3A-3D. IRDye 680LT goat anti-mouse was used at 1:3,000 (for probing by iBind) in FIG. 12 to detect actin. A horseradish peroxidase-conjugated anti-mouse secondary antibody (71045, EMD Millipore, Billerica, Mass.) diluted 1:5,000 was used for chemiluminescent-based detection in FIGS. 1D and 1E.

Virus growth curve. To determine the growth kinetics of rLCMV in FIG. 2B, 6-well plates were seeded with $1.9\times10^5$ Vero E6 cells per well. The following day the cells were infected with each respective rLCMV at an MOI of 0.01. Supernatants were collected at 12, 24, 36, 48, and 72 hr pi, clarified by centrifugation at 1,200 RPM for 5 minutes at 4° C., then titered by plaque assay.

Z-virus-like particle (VLP) release assay. To determine the release efficiency of the Y88 mutant Z proteins in FIG. 2E, $2\times10^5$ HEK293T cells or T-Rex HEK293 cells stably transduced with a tetracycline-inducible plasmid encoding WT or dominant negative EQ mutant VPS4B were seeded in a 12-well plate. The next day cells were transfected with 0.8 μg per well of pLCMV-Z WT, Z-G2A, -Z Y88F, -Z Y88E, or -Z Y88A using 0.8 μL of a 1 mg/mL solution of polyethylenimine per well. For the experiments shown in FIG. 12, VPS4B expression was induced with 1 μg/mL tetracycline at the time of transfection. The following day (24 hr post-transfection) cells and VLP-containing media (which had been clarified) were collected, lysed with Triton lysis buffer, and subjected to quantitative western blotting. For detection of Z from VLPs produced in VPS4B WT or DN cell lines, SBP-tagged Z was affinity purified from lysed VLP-containing media using magnetic streptavidin beads prior to quantitative western blot analysis. To calculate the percent VLP release we first normalized each Z protein value (from supernatants or cells) by the sum of all Z protein bands on a particular gel using known approaches. The percent VLP release was then calculated as the quotient of the Z protein quantity in VLPs divided by the quantity of Z in cells [($Z_{mut}$ VLP/$Z_{mut}$ cells)/($Z_{WT}$ VLP/$Z_{WT}$ cells)].

Plaque assay and measurement of plaque size and cytopathic effect. To measure infectious virus titers, a plaque assay was employed as follows. Six-well plates were seeded with $1\times10^5$ (LCMV and JUNV) or $1\times10^6$ (VSV) Vero E6 cells per well and the following day inoculated with 10-fold serial dilutions of virus in a total volume of 0.5 mL of Vero E6 growth medium. Following a 90 minute absorption at 37° C., the cells were overlaid with a solution of 0.7% agarose (20-102, Apex Industrial Chemicals, Aberdeen, United Kingdom) in Vero E6 growth media. The plates were fixed 2 (VSV) or 4 (LCMV and JUNV) days later with a solution of 2.5% formaldehyde (1635-4L, Sigma) in 3×PBS. Following removal of the agarose plugs, the fixed monolayers were stained with 0.1% crystal violet (C581-100, Fisher Scientific) and 2.1% ethanol in water. To determine the plaque size of rLCMV in FIG. 2D or the overall level of cytopathic effect induced by these viruses in FIGS. 4A, 4B, 6C, and 6D, the wells were imaged with an Alpha Innotech digital camera paired to a Computar H6Z0812M motorized zoom lens. The area of each plaque as well as the mean pixel intensity of each well was calculated using ImageJ software.

Plaque interference assay. To determine the titer of LCMV DI particles, samples were transferred to clear snap cap tubes (21-402-904, Thermo Scientific) and irradiated for 2 minutes with UV light in a UVP CL-1000 ultraviolet crosslinker in to kill standard infectious virus. The samples were serially diluted in 5-fold increments and added to 24-well plates which had been seeded the previous day with 20,000 (LCMV and JUNV C#1) or 100,000 (VSV) Vero E6 cells per well. Subsequently, 50 PFU per well of rLCMV WT (or 50 PFU per well of JUNV C#1 or VSV in FIG. 5A) was added to each well containing UV-irradiated samples. UV-irradiated samples were also added to a second set of wells to which no standard virus was added to ensure that all infectious virus had been eliminated from the samples. After a 90 minute absorption period at 37° C., the cells were overlaid with a solution of 0.7% agarose in Vero growth media and left at 37° C. The plates were fixed and stained 2 (VSV) or 4 (LCMV and JUNV C#1) days later as above for the plaque assay. The plaques were counted in each well and the plaque interfering unit 50 ($PIU_{50}$) was calculated using the plaque reduction statistical web tool (https://exon.niaid.nih.gov/plaquereduction). Because a unique biochemical or genetic signature to differentiate standard infectious virus particles from DI particles has not been defined, the assay we employed relied on measurement of the interfering activity of DI particles as opposed to a direct physical measure of the particles themselves. For FIG. 5B, rLCMV WT was filtered with either 0.45 μM (28145-481, VWR, Radnor, Pa.) or 0.2 μM (09-719C, Fisher Scientific) syringe filters or Amicon 30K (UFC903024, Millipore) or 10K (UFC901024, Millipore) centrifugal filters prior to treatment with UV light and DI titering as above.

Virus challenge in inducible VPS4A- and VPS4B-expressing cell lines. To determine the role of the ESCRT pathway in LCMV release, $2.5\times10^5$ T-Rex HEK293 cells stably transduced with a tetracycline-inducible VPS4A or VPS4B (WT or dominant negative EQ in each case) were seeded in 6-well plates that were first coated with poly D-lysine (P6407, Sigma-Aldrich) for 5 minutes then washed 3× with PBS. Cells were infected 24 hr later with rLCMV WT at an MOI of 0.001. Forty-eight hr later (when all cells were productively infected) the cells were induced with growth medium containing 1 μg/mL tetracycline or a medium only control. Six hr after induction cells were washed 3× with PBS and fresh growth medium containing 1 μg/mL tetracycline or medium alone were added. Eighteen hr later the cells and supernatants were collected. In FIGS. 6A and 6B, the cell lysates were probed for VPS4B DN or WT protein (via the GFP fusion tag on these proteins) or actin expression by quantitative western blotting. Supernatants were titered by plaque assay for infectious virus and DI particle levels by measuring the cytopathic effect in a plaque assay with equal PFUs of virus in each well (as described under plaque assay) and/or by plaque interference assay. The role of VPS4B in VSV release was also tested. For the VSV challenge studies, $5\times10^5$ VPS4B WT or EQ cells were seeded in poly D-lysine treated wells and 24 hr later treated with either growth medium containing 1 μg/mL tetracycline or medium alone. One hr later, the cells were infected with VSV at an MOI of 10. One hr following infection, the cells were washed 3× with PBS and fresh growth medium containing 1 μg/mL tetracycline or medium alone was added. Six hr later the cells and supernatants were collected and assessed by quantitative western blotting and plaque assays, respectively.

In order to verify uniform VPS4B expression as well as rLCMV WT infection by microscopy, in parallel to the experiment described above, $5\times10^4$ cells were seeded on poly D-lysine-treated 12 mm glass coverslips in 24-well plates. At the time of harvest (24 hr post-infection) the coverslips were rinsed with PBS, fixed with 4% paraformaldehyde (15714, Electron Microscopy Sciences, Hatfield, Pa.) in PBS for 20 minutes, then washed 2× with PBS for 5 minutes. The cells were permeabilized with 0.1% Triton X-100 in 1% bovine serum albumin (BSA) in PBS, blocked with 10% normal goat serum (005-000-121, Jackson, West Grove, Pa.) in 1% BSA in PBS, and immunostained with anti-LCMV nucleoprotein antibody (1.3-3) (1:500) and secondary anti-mouse Alexafluor 555 (A28180, Thermo Scientific) (1:1,000) each for 1 hr in 1% BSA in PBS. DNA was detected with 4', 6-diamidino-2-phenylindole hydrochloride (DAPI) (D9542, Sigma Aldrich) in 1% BSA in PBS. Cells were washed with 1% BSA in PBS in between each step. Images were acquired on a Zeiss LSM 510 laser scanning confocal microscope using a 63× objective lens. Post-capture image processing was carried out in FIJI and Photoshop; the GFP fluorescence, NP staining, and DAPI signal are shown at equal exposures in all conditions.

Virion concentration and fractionation. To determine the NP, GP, and Z protein content of rLCMV virions in FIGS. 3A-3D, $2\times10^6$ Vero E6 cells were seeded in a T-150 culture flask and infected the next day at an MOI of 0.01, 0.001, or 0.0001. At 48 or 72 hr following inoculation, the supernatant was collected, clarified by centrifugation, and screened for infectious virus by plaque assay. An equal number of plaque forming units of each virus (range 1 to $3\times10^7$ PFU per experiment) were layered onto a solution of 20% sucrose in THE buffer, pH 7.4 (10 mM Tris base, 1 mM EDTA, 0.2 M NaCl) and centrifuged for 2 hr at 30,000 rpm at 4° C. in a Thermo-Scientific Sorval WX Ultra 80 ultra centrifuge equipped with a Sorval Surespin 630 rotor. The resulting virus pellet was resuspended in 2×-concentrated Laemmli buffer containing 5% 2-mercaptoethanol, then analyzed by SDS-PAGE and quantitative western blotting.

To separate rLCMV by gradient centrifugation in FIG. 9, $2\times10^6$ Vero E6 cells were seeded in a T-150 culture flask and infected the next day at an MOI of 0.0001. At 72 hr following inoculation, the supernatant was collected and clarified by centrifugation. The clarified supernatants were added to 50 mL tubes (430290, Corning) containing polyethylene glycol (PEG) 8000 (81268, Sigma-Aldrich) and sodium chloride such that the final concentrations were 10% and 1%, respectively. The solutions were incubated at 4° C. on a rotating platform for 2 hr then were centrifuged for 30 minutes at 10,000 rpm at 4° C. in a Thermo-Scientific Sorval Legend RT+ centrifuge equipped with a Sorval Fiberlite F15-8x50cy rotor. The supernatant was removed and the virus-PEG pellet was resuspended in THE buffer and screened for infectious virus by plaque assay. Density gradients were prepared by layering solutions of 7%, 10%, 13%, 16%, and 19% optiprep (D1556, Sigma-Aldrich) diluted in PBS in 36 mL tubes (03141, Thermo Scientific) then leaving overnight at 4° C. to allow a continuous gradient to form. An equal number of plaque forming units of each virus (range $4\times10^7$ to $1\times10^8$ PFU per experiment) was layered onto the continuous gradient and centrifuged for 12 hr at 30,000 rpm at 4° C. in a Thermo-Scientific Sorval WX Ultra 80 ultracentrifuge equipped with a Sorval Surespin 630 rotor. The resulting separated virus was collected in 2 mL fractions using a New Era NE-9000G programmable peristaltic pump and titered via plaque assay.

Quantitative RT-PCR. To enumerate copies of LCMV S and L segment genomic RNA contained in virions for FIGS. 3E and 3F, viral RNA was extracted from cell-free virions using the Qiagen Viral RNA mini kit according to the manufacturer's instructions and subjected to quantitative RT-PCR using known approaches. Briefly, cDNA was generated in a 50 µL RT reaction containing 5 µL of viral RNA, 0.2 µM of the gene specific primer S 2865-(5'-CAGGGTGCAAGTGGTGTGGTAAGA-3') (SEQ ID NO:35) or L 5906-(5'-TGGGACTGAGTTTCGAGCAT-TACG-3'), (SEQ ID NO:36) which are complementary to the S or L segment genomic RNA, 5 µL of 10×PCR Buffer II (#E12874, Applied Biosystems, Carlsbad, Calif.), 5 µL of 10 mM dNTP mix (362275, Applied Biosystems), 1 µL RNase inhibitor (N808-0119, Applied Biosystems), and 1.25 µL of Multiscribe reverse transcriptase (4308228, Applied Biosystems). RT reaction conditions were 25° C. for 10 minutes, 48° C. for 30 minutes, and 95° C. for 5 minutes. Quantitative PCR was then performed in a 25 µL reaction volume consisting of 5 µL of cDNA, 0.9 µM each of the forward primer S 2275+(5'-CGCTGGCCTGGGTGAAT-3') (SEQ ID NO:37) or L 5517+(5'-GGCCTTGTATG-GAGTAGCACCTT-3') (SEQ ID NO:38) and reverse primer S 2338-(5'-ATGGGAAAACACAACAATTGATCTC-3') (SEQ ID NO:39) or L 5645-(5'-GGTCTGTGAGATAT-CAAGTGGTAGAATG-3'), (SEQ ID NO:40) 0.2 µM of the TaqMan probe S 2295+(5'-6FAM-CTGCAGGTTTCTCGC-MGBNFQ-3') (SEQ ID NO:41) or L 5582-(5'-6FAM-CT-GAAGAATACCACCTATTATACCA-MGBNFQ-3'), (SEQ ID NO:42) and 12.5 µL of the TaqMan Universal PCR Master Mix (4326614, Life Technologies, Grand Island, N.Y.). Reaction conditions were 95° C. for 10 minutes followed by 40 cycles of 95° C. for 15 seconds and 60° C. for 1 minute. Copy numbers of LCMV S or L segment genomic RNAs were calculated by comparison with a series of standard dilutions of the pT7-S or pT7-L plasmids. Data was generated on an Applied Biosystems StepOnePlus Real-Time PCR System and analyzed with the provided software.

Statistical analysis. Statistical analysis was performed using GraphPad Prism software. For the virus growth curves in FIG. 2B, the data was first log transformed, then a two-way analysis of variance (ANOVA) was performed with a Holm-Sidak's test for multiple comparisons to compare viruses at each time point. A one-way ANOVA with Holm-Sidak's test for multiple comparisons was used to analyze the VLP release assay in FIG. 2E, the viral protein levels in concentrated virions in FIGS. 3B-3D, and the S and L segment to PFU ratios in FIGS. 3E and 3F. To compare plaque area in FIG. 2D, the data were first tested for normality using the D'Agostino and Pearson omnibus normality test, then the Kruskal-Wallis non-parametric test was used and multiple comparisons were made with Dunn's multiple comparisons test. To analyze the cytopathic effect induced by rLCMV WT or Z-Y88 mutants (FIG. 4B) or by rLCMV WT generated in VPS4B WT or dominant negative cells (FIG. 6D), a two-way ANOVA was performed with the Holm-Sidak's test for multiple comparisons. To compare VSV or LCMV virus titers, LCMV DI particle titers, or Z VLP levels produced in VPS4B WT or EQ cells (FIGS. 6A, 6B, and 6E) a two-tailed unpaired t test with Welch's correction was performed. To compare DI particle titers in FIGS. 5A-5C, a value of 19 $PIU_{50}$/mL (just below the limit of detection value of 20 $PIU_{50}$/mL) was substituted for samples that were below the limit of detection and then a one way ANOVA was performed. For all statistical analyses, the data utilized was generated from at least 3 independent experiments as indicated in each respective figure legend.

This Example and its accompanying figured demonstrate that LCMV matrix protein is phosphorylated at serine 41. A recombinant (r)LCMV bearing a phosphomimetic mutation (S41D) was impaired in infectious and defective interfering (DI) particle release while a nonphosphorylatable mutant (S41A) was not. The S41D mutant was disproportionately impaired in its ability to release DI particles relative to infectious particles.

To screen for phosphorylation sites in LCMV Z, we transfected HEK-293T cells with a plasmid encoding the LCMV strain Armstrong Z protein fused to a C-terminal streptavidin binding peptide (SBP) and subsequently used magnetic streptavidin beads (as described in Examples 1-7 to affinity purify SBP-tagged Z from the transfected cells as well as from VLPs that had been released into the tissue culture media. Purified Z-SBP was separated by SDS-PAGE (FIG. 13(a)), prepared for mass spectrometry analysis by in-gel tryptic digestion, and analyzed by liquid chromatography-mass spectrometry essentially as described in Examples 1-7. This analysis revealed a novel serine phosphorylation site at S41 in Z-transfected cells (FIG. 13(b)). S41, a site conserved in the Old Word arenaviruses Dandenong and Ippy (FIG. 13(d)), is located in the central really interesting new gene (RING) domain of Z (FIG. 13(c)) and is outside of any motif known to be important for arenavirus budding and release.

To determine the importance of the S41 residue for viral fitness, recombinant (r)LCMV containing a nonphosphorylatable alanine (S41A) or a phosphomimetic aspartic acid (S41D) substitution at position 41 were recovered using reverse genetics as described for Examples 1-7. Initially, it appeared that the S41D phosphomimetic mutant could not be recovered as it did not produce plaques in a standard plaque assay (FIG. 14(a)). However, staining for viral nucleoprotein (NP) via immunofocus assay revealed that the S41D mutant was recoverable despite its inability to form plaques (FIG. 14(a)). Growth curve analysis revealed that the phosphomimetic S41D virus was attenuated in its growth kinetics while the nonphosphorylatable S41A mutant grew to similar levels as wild type (FIG. 14(b)). The attenuation of the S41D mutant was also apparent in the smaller foci it formed, which were less than 50% of WT size (FIGS. 14(a) and (c)). To determine whether the reduction in infectious titer of the phosphomimetic S41D virus was due to decreased virus budding and release, we employed a Z VLP release assay as described for Examples 1-7 and found that the budding efficiency of the phosphomimetic Z-S41D was reduced ~60% while the budding activity of the nonphosphorylatable S41A was not different from WT (FIG. 14(d)). Collectively, these findings demonstrate that the S41 residue possesses a previously unappreciated capacity to drive virus budding and that this function may be regulated by phosphorylation.

As the reduction in VLP release by Z-S41D (FIG. 14(d)) did not appear to fully explain the greater than 10-fold reduction in virus titer observed in FIG. 14(b), we probed rLCMV WT or S41 mutant virion preparations for structural protein and/or genome deficits. To determine the composition of each virus particle preparation, an equal number of focus forming units (FFU) of cell-free rLCMV WT, S41A, or S41D viruses were concentrated through a 20% sucrose cushion by ultracentrifugation as described for Examples 1-7 and virion protein quantity was analyzed by quantitative western blotting (FIGS. 15(a) to (d)). The S41D phosphomimetic virus preparation, despite containing equivalent infectious units as the WT and S41A preparations, had markedly reduced levels of NP, glycoprotein, and Z (FIG. 15(a) to (d)). Interestingly, the quantities of viral genomic S and L segment RNAs, measured by quantitative polymerase chain reaction (PCR) as described for Examples 1-7 did not differ between the preparations of WT, S41A, or S41D viruses (FIGS. 15(e) and (f)). The loss in viral structural protein content without a corresponding loss in infectious titer led us to hypothesize that the S41D phosphomimetic virus may be defective in its ability to generate DI particles, which could explain the reduced levels of viral protein observed relative to infectious units. To test whether S41 can indeed act as a regulatory motif to control DI particle production, we infected Vero E6 cells with rLCMV WT, S41A, or S41D and 72 hours later measured infectious virus levels by immunofocus assay and DI particle activity by a plaque interference assay as described for Examples 1-7. All three viruses had approximately equivalent titers of infectious virus (FIG. 15(g)). The DI particle titer of the S41D phosphomimetic virus, however, was reduced greater than 10-fold compared to WT virus while the DI particle titer of the S41A virus was not different from WT (FIG. 15(h)). These results indicate that the loss of viral structural protein content observed in the phosphomimetic S41D virus preparation (FIGS. 15(a)-(d)) was likely due to the reduced production of DI particles, not infectious virus particles.

The S41 phosphomotif represents a novel regulatory site within the LCMV Z protein. We recently demonstrated that the PPXY late domain in LCMV Z is not absolutely required for the production of infectious LCMV virions as described for Examples 1-7. Provided that the only other motif in Z with a known role in budding activity is the myristoylation site at the glycine at position 2 (FIGS. 13(c) and 14(d)) our finding here expands the functional repertoire of motifs in LCMV Z that regulate the efficiency of infectious virus release. Further, this Example builds upon Examples 1-7 by showing that S41 also serves as a key regulator of DI particle formation. To our knowledge, these are the only two motifs known to specifically regulate DI particle formation over standard particles for any virus family. Further, our findings support the hypothesis that phosphorylation of Z is an important mechanism by which the virus can adjust its rate of DI particle formation in response to the dynamic environment of the host cell (e.g. phosphorylation at Y88 appears to increase DI particle production whereas phosphorylation of S41 represses it (FIG. 15(h)).

While the disclosure has been particularly shown and described with reference to specific embodiments, it should be understood by those having skill in the art that various changes in form and detail may be made therein without departing from the spirit and scope of the present disclosure as disclosed herein.

What is claimed is:

1. A modified arenavirus comprising an introduced heterologous PPXY domain.

2. The modified arenavirus of claim 1, wherein the modified arenavirus comprises the introduced PPXY domain, and wherein the modified arenavirus is a modified Old World arenavirus.

3. The modified arenavirus of claim 1, wherein the modified arenavirus is produced by cells that comprise a kinase inhibitor that is not made by the cells and which inhibits a kinase that can phosphorylate the Y amino acid of the heterologous introduced PPXY domain.

4. The modified arenavirus of claim 3, wherein the modified arenavirus is produced by the cells that comprise the kinase inhibitor.

5. The modified arenavirus of claim 3, wherein the modified arenavirus is present in a pharmaceutical formulation.

6. An isolated cell culture comprising a population of arenaviruses, wherein the cells are infected with arenavirus wherein the cells are characterized by a modification such that expression of a kinase capable of phosphorylating a tyrosine in an introduced heterologous PPXY domain of the arenavirus is inhibited or eliminated.

* * * * *